United States Patent
Li et al.

(10) Patent No.: US 11,181,978 B2
(45) Date of Patent: Nov. 23, 2021

(54) SYSTEM AND METHOD FOR GAZE ESTIMATION

(71) Applicant: City University of Hong Kong, Kowloon (HK)

(72) Inventors: Youfu Li, Kowloon (HK); Dan Su, Kowloon (HK)

(73) Assignee: hemy8 SA, Morges (CH)

(*) Notice: Subject to any disclaimer, the term of this patent is extended or adjusted under 35 U.S.C. 154(b) by 0 days.

(21) Appl. No.: 16/442,765

(22) Filed: Jun. 17, 2019

(65) Prior Publication Data

US 2020/0393896 A1    Dec. 17, 2020

(51) Int. Cl.
| | |
|---|---|
| *G06F 3/01* | (2006.01) |
| *A61B 3/113* | (2006.01) |
| *G06T 7/73* | (2017.01) |
| *G06K 9/00* | (2006.01) |
| *G02B 27/00* | (2006.01) |

(52) U.S. Cl.
CPC .............. *G06F 3/013* (2013.01); *A61B 3/113* (2013.01); *G02B 27/0093* (2013.01); *G06K 9/00604* (2013.01); *G06T 7/74* (2017.01); *G06T 2207/30201* (2013.01)

(58) Field of Classification Search
CPC . G06F 3/013; G06T 2207/30201; G06T 7/74; G02B 27/0093; G06K 9/00604
USPC ........................................................ 382/103
See application file for complete search history.

(56) References Cited

U.S. PATENT DOCUMENTS

| | | | |
|---|---|---|---|
| 9,041,787 B2 | 5/2015 | Andersson et al. | |
| 9,164,583 B2 | 10/2015 | Williams et al. | |
| 9,213,406 B2 | 12/2015 | Ou-Yang et al. | |
| 10,223,808 B2 | 3/2019 | Hoffmann et al. | |
| 10,307,053 B2 | 6/2019 | Fayolle | |
| 2005/0058337 A1* | 3/2005 | Fujimura | G06K 9/32 382/159 |
| 2013/0222384 A1* | 8/2013 | Futterer | G03H 1/26 345/426 |
| 2018/0133593 A1 | 5/2018 | Wilson | |
| 2019/0121427 A1* | 4/2019 | Qin | G06F 3/013 |
| 2019/0354172 A1* | 11/2019 | Davies | G06F 3/013 |
| 2020/0027275 A1* | 1/2020 | Wan | G06T 17/05 |

OTHER PUBLICATIONS

Fathi, Alireza, Yin Li, and James M. Rehg. "Learning to recognize daily actions using gaze." European Conference on Computer Vision. Springer, Berlin, Heidelberg, 2012. (Year: 2012).*
Su, Dan, et al, "Development of Precise Mobile Gaze Tracking System Based on Online Sparse Gaussian Process Regression and Smooth-Pursuit Identification". In Proc. ROBIO., IEEE 2017.

(Continued)

*Primary Examiner* — Amandeep Saini
(74) *Attorney, Agent, or Firm* — Renner Kenner Greive Bobak Taylor & Weber

(57) ABSTRACT

A method for gaze estimation. The method includes processing training data and determining one or more local-learning base gaze estimation model based on the training data. The local-learning base gaze estimation model(s) can be used for determining one or both of: 2D gaze points in a scene image and 3D gaze points in scene camera coordinates.

32 Claims, 17 Drawing Sheets

(56) References Cited

OTHER PUBLICATIONS

Su, Dan, et al, "Toward Flexible Calibration of Head-Mounted Gaze Trackers with Parallax Error Compensation". In Proc. ROBIO., IEEE, 2016.
Bernet, Sacha, et al. "Study on The Interest of Hybrid Fundamental Matrix for Head Mounted Eye Tracker Modelin", In Proc. BMVC., 2011.

* cited by examiner

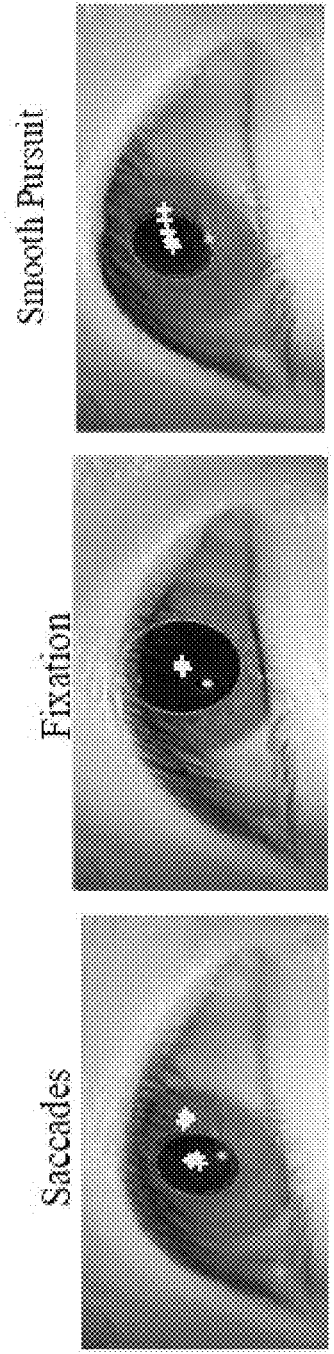
Figure 3A
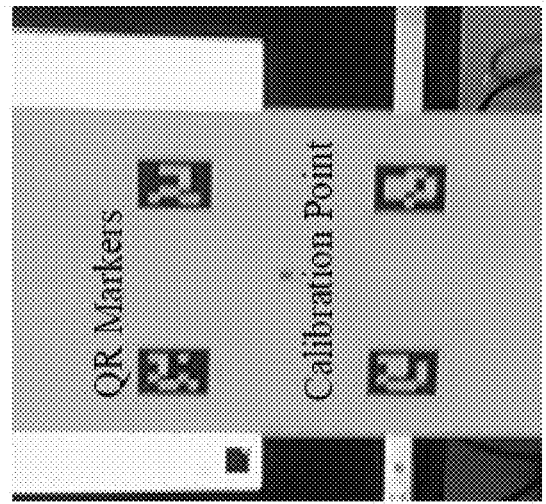
Figure 3C
Figure 3B

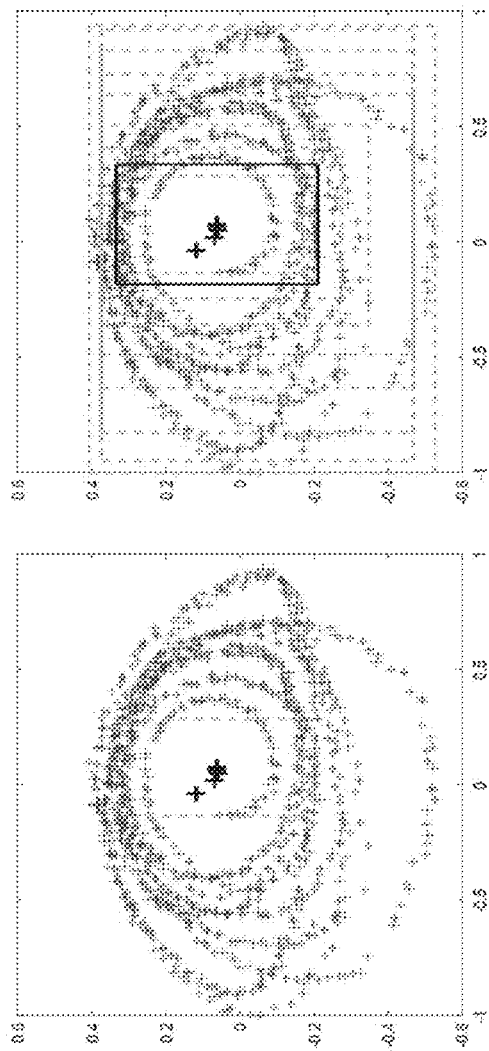
Figure 5B
Figure 5A
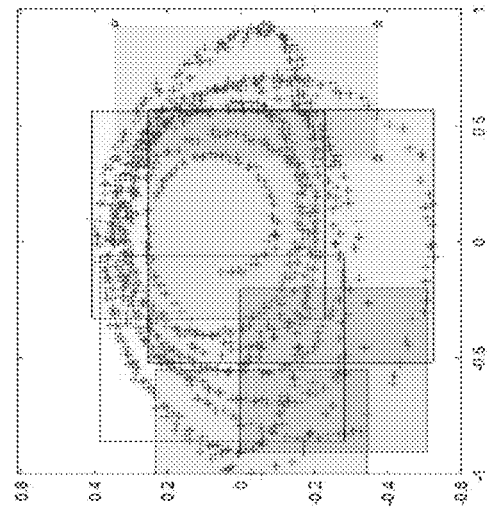
Figure 5D
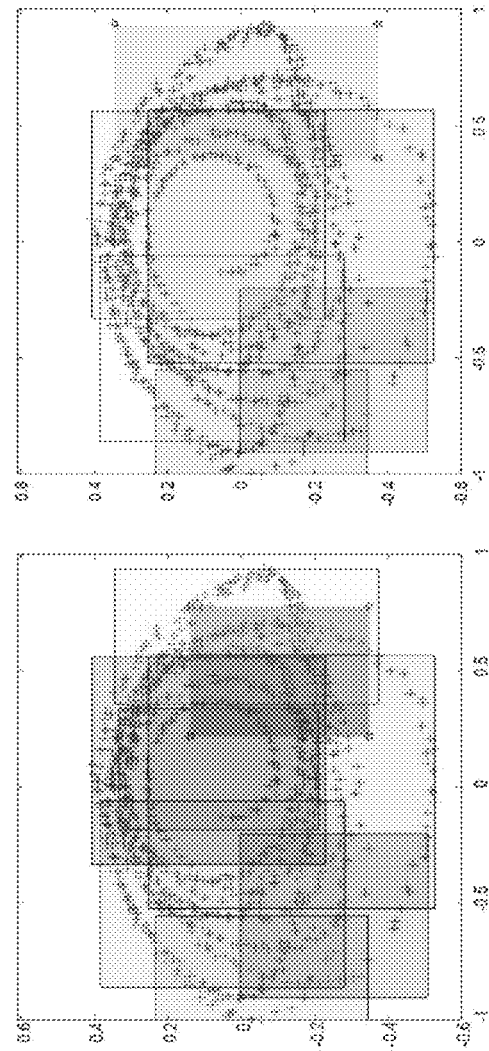
Figure 5C

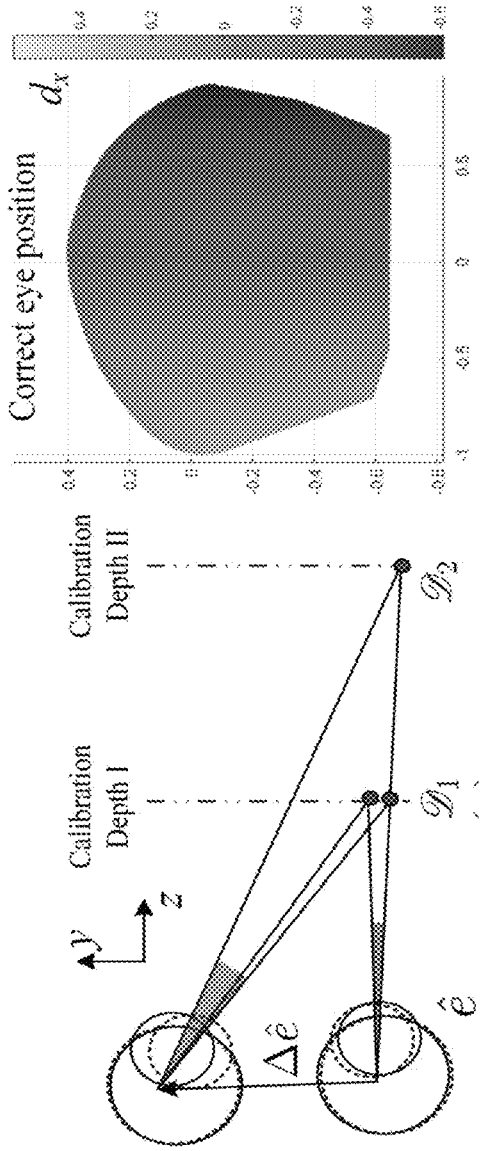
Figure 6A
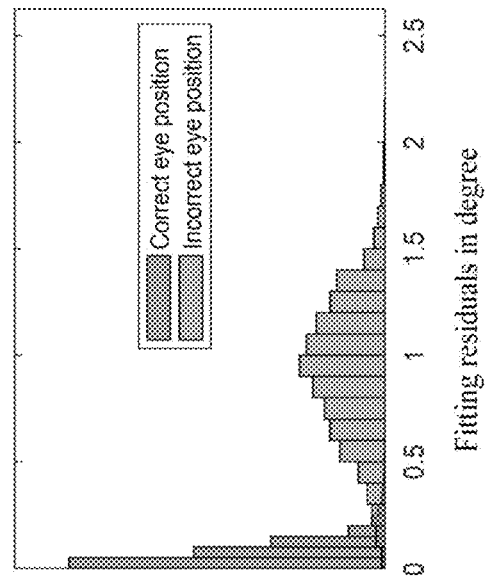
Figure 6B
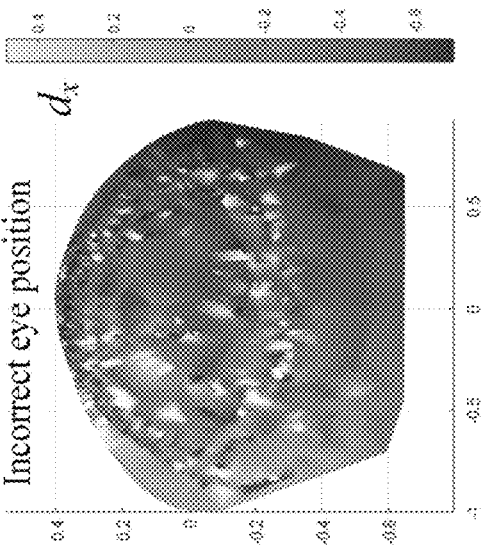
Figure 6C
Figure 6D

SYSTEM AND METHOD FOR GAZE ESTIMATION

TECHNICAL FIELD

The invention relates to systems and methods for gaze estimation.

BACKGROUND

Gaze tracking technique can be used to determine where the user is looking at by monitoring, in real-time, the eye motions of freely-moving users. This technique is a useful tool in human-machine interactions.

In tracking using mobile head-mounted gaze trackers (HMGT), a scene camera and eye cameras are used to capture the user's viewing field and to observe the user's eye motions, respectively. Generally, in this type of tracking, there are two kinds of gaze estimation outputs. The first one is 2D point of regard (POR) on the scene camera image; the second one is 3D POR in the scene camera or world coordinates. Theoretically, 3D PORs can be directly recovered by calculating the intersection point between the 3D environment map and the back-projection ray of 2D gaze points. Nonetheless, this kind of method typically requires an RGB-D camera to reconstruct dense 3D structures. Alternatively, 3D PORs can be computed as the middle point between two visual axes, which is useful even with the knowledge of reconstructed environments. For example, gaze depths inferred from visual axes can assist in localizing and determining the correct interested object (object that the user is looking at) when the 2D POR lies close to the image boundary of multiple objects.

For predicting 2D POR on the scene image, a regression model is specified to register the pupil centers with 2D PORs. However, if an improper regression model is used, the 2D POR estimation would suffer from parallax errors caused by the spatial offset between the scene camera projection point and the eyeball center. Meanwhile, a noticeable interpolation/extrapolation error may occur due to the under-fitting phenomena caused by some global parametric models. This or similar under-fitting problem is confronted by some regression-based methods developed for the 3D visual axis prediction. Alternatively, model-based gaze tracking methods can be used. This type of model-based gaze tracking methods has several merits, including a rapid one-point calibration process and robustness against the system drift. Nonetheless, this kind of methods either requires complex hardware configuration or is dependent on a simplified eye model (which could yield significant angular errors). Also, the model-based approaches typically assume the population-average physiological parameters, which might give rise to the performance degrade in cases of eyewear users (user with eye disorder such as myopia, hyperopia, etc.). Considering the above, the regression-based approach is, in some applications, a better option as it does not require a precise eye model.

Moreover, for both the model-based and regression-based approaches, the eyeball positions in the scene camera space should be learned. Some high-end HMGTs address this issue by employing fully calibrated geometrical systems. On the other hand, for low-cost HMGTs, the eyeball positions can be estimated by formulating a nonlinear optimization problem that aims to reduce the angular differences between the training gaze direction and prediction ones. However, existing commonly-used unconstrained optimization may provide an erroneous eye position, which leads to unsatisfactory generalization capacities.

SUMMARY OF THE INVENTION

In accordance with a first aspect of the invention, there is provided a method for estimating gaze point, comprising: processing training data; and determining one or more local-learning based gaze estimation model based on the training data, for determining one or both of: (i) 2D gaze points in a scene image and (ii) 3D gaze points in scene camera coordinates.

In one embodiment of the first aspect, the method also includes determining 2D gaze points in the scene image.

In one embodiment of the first aspect, the method also includes determining 3D gaze points in the scene camera coordinates.

In one embodiment of the first aspect, the method also includes obtaining data for determining the training data.

In one embodiment of the first aspect, obtaining the data comprises recording movement trajectories of pupil centers of a user's eyes and one or more movement trajectories of respective calibration points in a scene image at a first calibration depth, the calibration point being gazed at by the user.

In one embodiment of the first aspect, the recording is performed as the user changes head pose.

In one embodiment of the first aspect, the recording is performed as the user rotates the head.

In one embodiment of the first aspect, the recording is performed for at least two rotations of the user's head.

In one embodiment of the first aspect, obtaining the data further comprises obtaining 3D position of the calibration point.

In one embodiment of the first aspect, obtaining the data comprises recording movement trajectories of pupil centers of a user's eyes and one or more movement trajectories of respective calibration points in a scene image at a second calibration depth different from the first calibration depth, the calibration point being gazed at by the user. The first calibration depth ($D_1$) and/or the second calibration depth ($D_2$) are selected based on a difference of their reciprocals, i.e., $1/D_1 - 1/D_2$. Generally, the larger the value of $1/D_1 - 1/D_2$, the better the calibration precision.

In one embodiment of the first aspect, the recording is performed as the user changes head pose.

In one embodiment of the first aspect, the recording is performed as the user rotates the head.

In one embodiment of the first aspect, the recording is performed for at least two rotations of the user's head.

In one embodiment of the first aspect, obtaining the training data further comprises obtaining 3D position of the calibration point.

In one embodiment of the first aspect, the method also includes identifying eye smooth pursuit movement performed by the user during data recording, based on the data obtained.

In one embodiment of the first aspect, the method also includes preserving data recorded during eye smooth pursuit movement. Preferably, only the data recorded during eye smooth pursuit movement is preserved and used for subsequent processing and analysis (e.g., inclusion in the training data). In other words, data recorded during types of eye movement is not used for subsequent processing and analysis.

In one embodiment of the first aspect, the method also includes performing principal component analysis on the data obtained to identify eye smooth pursuit movement.

In one embodiment of the first aspect, the method also includes partitioning input space into a plurality of sub-regions.

In one embodiment of the first aspect, the method also includes determining a local-learning base gaze estimation model for each of the sub-regions based on the learning data.

In one embodiment of the first aspect, the determination of the local-learning base gaze estimation model is based on polynomial lens distortion model.

In one embodiment of the first aspect, the method also includes determining a coverage area of the sub-region.

In one embodiment of the first aspect, the sub-regions are rectangular, preferably axis-aligned rectangular.

In one embodiment of the first aspect, the sub-regions comprise multiple overlapping sub-regions.

In one embodiment of the first aspect, determining a coverage area of the sub-region comprises: gradually expanding the coverage area to cover more training data; and terminating the expansion process as the condition of reaching minimal leave-one-out prediction error.

In one embodiment of the first aspect, the method also includes determining eyeball center position and back-projection matrices for each of the sub-regions.

In one embodiment of the first aspect, the determination of the eyeball center position and back-projection matrices for each of the sub-regions is based on solving a constrained nonlinear optimization problem.

In accordance with a second aspect of the invention, there is provided a system for gaze estimation, comprising: one or more processors arranged to process training data; and determine one or more local-learning base gaze estimation model based on the training data, for determining one or both of: (i) 2D gaze points in a scene image and (ii) 3D gaze points in scene camera coordinates.

In one embodiment of the second aspect, the system includes a wearable device with two eye movement monitors (e.g., cameras) and an imaging sensor that senses the scene image.

In one embodiment of the second aspect, the system is arranged to perform the method of the first aspect.

BRIEF DESCRIPTION OF THE DRAWINGS

Embodiments of the invention will now be described, by way of example, with reference to the accompanying drawings, in which:

FIG. 3A shows images of an eye illustrating 3 different kinds of eye movements (saccades, fixation, and smooth pursuit), wherein the crosses in the eye images denote the pupil centers captures in multiple consecutive frames;

FIG. 3B shows the two principal axes of the cluster holding mean-centered pupil centers for the smooth pursuit eye movement in the corresponding image in FIG. 3A;

FIG. 3C shows the calibration pattern for obtaining training data in one embodiment of the invention;

FIG. 5A shows a cross-validated partition of the pupil center space at a first point of a partition algorithm in one embodiment of the invention;

FIG. 5B shows the cross-validated partition of the pupil center space of FIG. 3A at a second point of the partition algorithm in FIG. 5A;

FIG. 5C shows the cross-validated partition of the pupil center space of FIG. 3A at a third point of the partition algorithm in FIG. 5A;

FIG. 5D shows the cross-validated partition of the pupil center space of FIG. 3A at a fourth point of the partition algorithm in FIG. 5A;

FIG. 6A shows the fitting residuals with an incorrect estimation on eye position e;

FIG. 6B shows the surface created by training pairs with correct eye position;

FIG. 6C shows the surface created by training pairs with misaligned eye position;

FIG. 6D is a histogram of residuals when fitting the training data by the region-wise polynomial regression in one embodiment of the invention;

DETAILED DESCRIPTION OF THE PREFERRED EMBODIMENT

The present invention provides a novel region-wise learning model for 2D and 3D POR estimation with mobile gaze trackers, and system and methods for implementing such model. The learning model is motivated from the idea that the input space of pupil centers can be clustered into a set of sub-regions such that simple local models are sufficient to fit the training data in each sub-region.

Figure 1:
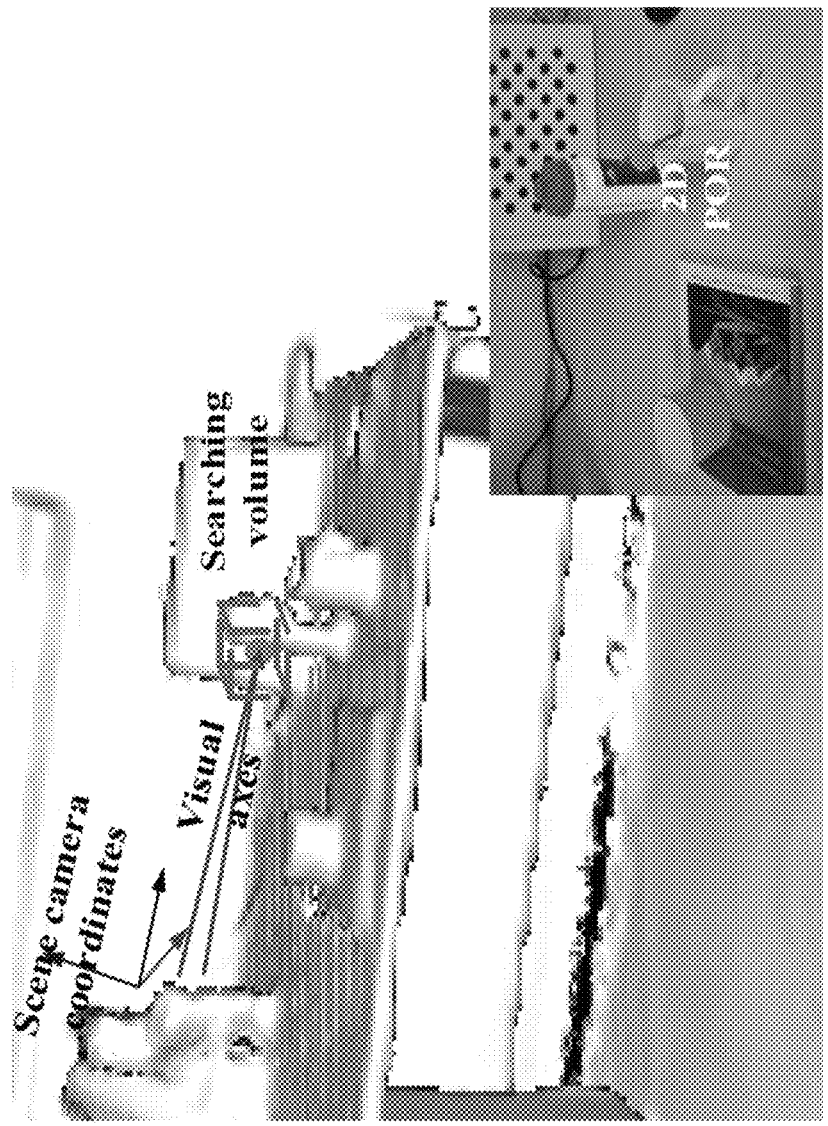
FIG. 1 is an illustration illustrating the 3D POR determined by two visual axes and the corresponding 2D POR on an object in one embodiment of the invention.

Referring to FIG. 1, for each local model, an epipolar line and a visual axis are predicted given a pupil center, thus 2D and 3D PORs can be calculated as the intersection point of two epipolar lines and visual axis, respectively.

In the region-wise learning model in one embodiment of the invention, a local homography-like relation is initially learned for fitting one-depth gaze data. This allows the fast computation of the Leave-One-Out (LOO) errors. Then, the partitioning structure can be determined in a cross-validated manner. The parallax errors observed at another (second) calibrated depth are used to restore the epipolar point position. Correspondingly, a point-to-line relationship can be inferred based on the epipolar point and homography-like mapping. As the same local projection approximation is adopted, the 3D model shares the same space partitioning structure as the corresponding 2D model. Then, a constrained nonlinear optimization problem is formulated to derive the 3D eyeball center and back-projection mapping for each region. Given the epipolar point in the 2D model, the nonlinear optimization is initialized with the rough estimation of the eyeball center. Depending on the optimization results, the visual axes of both eyes can be estimated from a suitable local model, and the 3D gaze point can be inferred as the point closest to two visual axes. To aid practical implementation, the strategy to set a sensible constraint for eyeball positions and to select the spatial distribution of calibration points, both of which are paramount to ensure the model learning accuracy, are explored.

I. Model Formulation

Considering actual optics of the cornea and reflection of corrective lenses, it is not a trivial task to precisely describe the global relationship between observed pupil centers and the user's visual axes. Intuitively, directions of visual axes change continuously with respect to the pixel coordinates of pupil centers. From this perspective, a simple polynomial function can approximate the gaze model in a local manner with sufficient precision. Given the input partition structure with N local regions $\{R_{(n)}, n \in 1 \ldots N\}$, Equation (1) is selected as the local model to link the image pupil center $p=[p_x\ p_y]^T$ with the visual rays $D(p)$, which is mathematically equivalent to the polynomial model applied in the camera un-distortion technique.

$$d(p) = \begin{bmatrix} d_x \\ d_y \\ d_z \end{bmatrix} \sim \begin{bmatrix} A^x_{(n)} \mathcal{X}(p) \\ A^y_{(n)} \mathcal{X}(p) \\ 1 \end{bmatrix}, \text{if } p \in \mathcal{R}_{(n)} \quad (1)$$

where $A^x_{(n)}$ and $A^y_{(n)}$ are 1×6 matrices, $\chi$ is defined as the "lifting" coordinates of the image pupil center, i.e., $\chi(p)=[1, p_x, p_y, p^2_x, p^2_y, p_{xy}]$. Thus, 3-D POR can predicted as a space point closest to two visual axes originating from the eyeball centers.

Meanwhile, considering the fact that the calibration surface is nearly parallel to the scene camera image plane, affine transform can be used to approximate the homography associating visual directions with the image PORs h(p). Thus, a homography-like relationship can be parameterized by 1×6 matrices $B^x_{(n)}$ and $B^y_{(n)}$ as follows:

$$h(p) = \begin{bmatrix} h_x \\ h_y \end{bmatrix} = \begin{bmatrix} B^x_{(n)} \mathcal{X}(p) \\ B^y_{(n)} \mathcal{X}(p) \end{bmatrix}, \text{if } p \in \mathcal{R}_{(n)} \quad (2)$$

Figure 2:
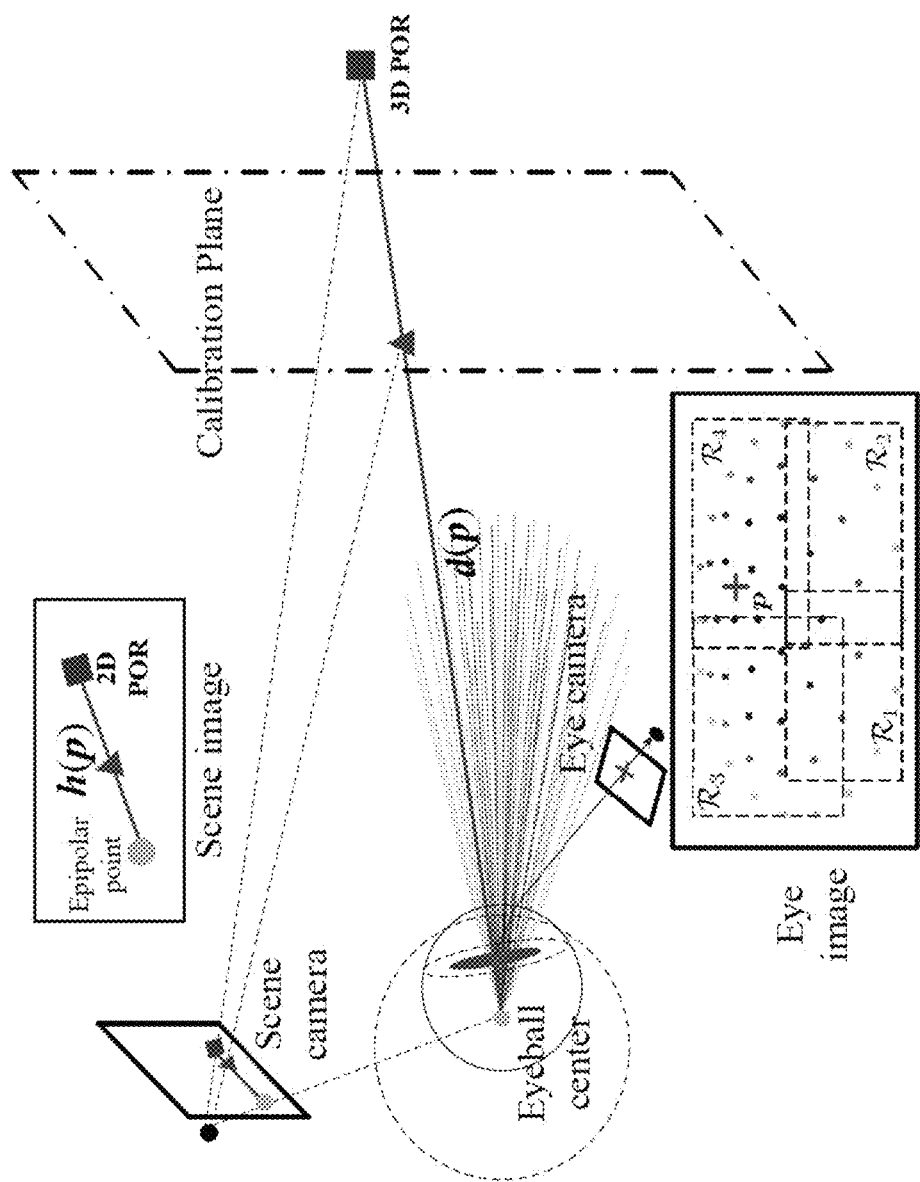
FIG. 2 is a schematic showing a region-wise polynomial model for gaze direction approximation in one embodiment of the invention.

This turns out to be consistent with the commonly-used image POR mapping function. As shown in FIG. 2, an epipolar line l*(p) (i.e., the image visual axis), which is determined by connecting the image eyeball center $[e_x\ e_y]$ and the 2-D virtual POR inferred by homography-like relation, can be calculated as follows:

$$l(p)=[e_x,e_y,1] \otimes [h(p)1] \quad (3)$$

where h(p) denotes the virtual POR predicted by Equation (2) and $\square$ is the cross product between two vectors. And a 2-D POR can be computed by intersecting two epipolar lines inferred from binocular data.

From Equations (1) and (4), it can be noted that 2-D and 3-D PORs can be measured with the region-wise model if (a) the image and space eyeball centers can be estimated; (b) the coefficient matrices $A_{(n)}$ and $B_{(n)}$ for each local area are resolved; (c) the entire input space can be reasonably clustered into multiple sub-regions with considerable local approximation accuracy. A cross-validated approach is particularly suitable for determining the locality. Fortunately, it can be observed from Equation (2) that the adopted polynomial models can be characterized as the linear mapping from the lifted coordinates of the image points, which allows the fast computation of the Leave-One-Out errors. In the following, a calibration framework to learn the input partition structure and 2D/3D model parameters will be presented.

II. Calibration for 2-D and 3-D Gaze Models

A. Training Data Preparation

Regarding the training data acquisition approach: in one embodiment of the invention, basically, the user is required to fixate at a single calibration point while smoothly rotating his/her head. This kind of the eye-head motion preferably has to be performed twice by placing the calibration point at two different depths $D_1$ and $D_2$.

Problematically, however, it cannot be guaranteed that the user will keep his attention on the calibration point during the whole calibration process. As a result, distractions and involuntary eye movements should be allowed during the calibration. In one embodiment, to compensate for smooth and persistent head movements, the eye smooth pursuit system will be activated to stabilize the image of the calibration point at almost the same position on the retina. Relevant neurology studies have shown that users can hardly perform eye movement in a smooth fashion without visual cues. Instead, without visual cues, the user will make a saccadic eye movement. In other words, the user is unlikely to scan a textureless region with smooth pursuit eye movements.

Based on this understanding, a calibration pattern at which the user will have to look at is designed as shown in FIG. 3C. As shown in FIG. 3C, the calibration pattern includes 4 QR markers and a middle (red) calibration point arranged centrally between the markers. Textureless white regions are arranged between the calibration point and the markers. Consequently, when the smooth pursuit eye movement is detected, it is safe to claim that the user's POR is not locating on the white textureless area.

Based on empirical observations, the prediction error of the polynomial mean function is typically bounded by 5-7 degrees. Thus, if the POR predicted by the polynomial mean function is close to the image calibration point and the smooth pursuit eye motion is detected, it can be concluded that the user is gazing at the calibration point and the corresponding gaze data can be identified as the reliable training data.

Consequently, the $i^{th}$ sampled data $\{p^{(i)}, y^{(i)}\}$ is considered as the inlier training data if it satisfies $$\|y^{(i)} - h(p^{(i)})\|_2 < \lambda$$

and $p^{(i)}$ is in smooth pursuit where $\lambda$ refers to a threshold determined by the area of textureless region centered at the calibration point.

Then, the smooth pursuit eye movements have to be recognized. Here a query tracklet $\Omega$ is defined as a collection of consecutive n samples in pupil trajectories. By investigating on the properties of three different eye motions (saccades, fixation, and smooth pursuit) shown in FIG. 3A, it can be noted that (a) the position of the pupil center $\upsilon$ will abruptly change in saccades movements; (b) compared with fixation, a query tracklet of the smooth pursuit should have the larger space variance and more notably different lengths in principal axes of the cluster of mean-centered pupil centers. Hence, the user is considered to take the smooth pursuit eye motion when $$\begin{cases} \sigma_2/\sigma_1 < \tau_{pursuit} \\ \sigma_2^2 + \sigma_1^2 > \tau_{var} \\ \max_{i \in \Omega} \|p^{(i)} - p^{(i-1)}\|_2 < \tau_{saccades} \end{cases}$$

where $\sigma_1$ and $\sigma_2$ are the largest and the second largest singular values of the matrix holding the mean-centered pupil centers in the query tracklet $\Omega$, $\tau_{saccades}$, $\tau_{var}$ and $\tau_{pursuit}$ are predefined thresholds.

Figure 4:
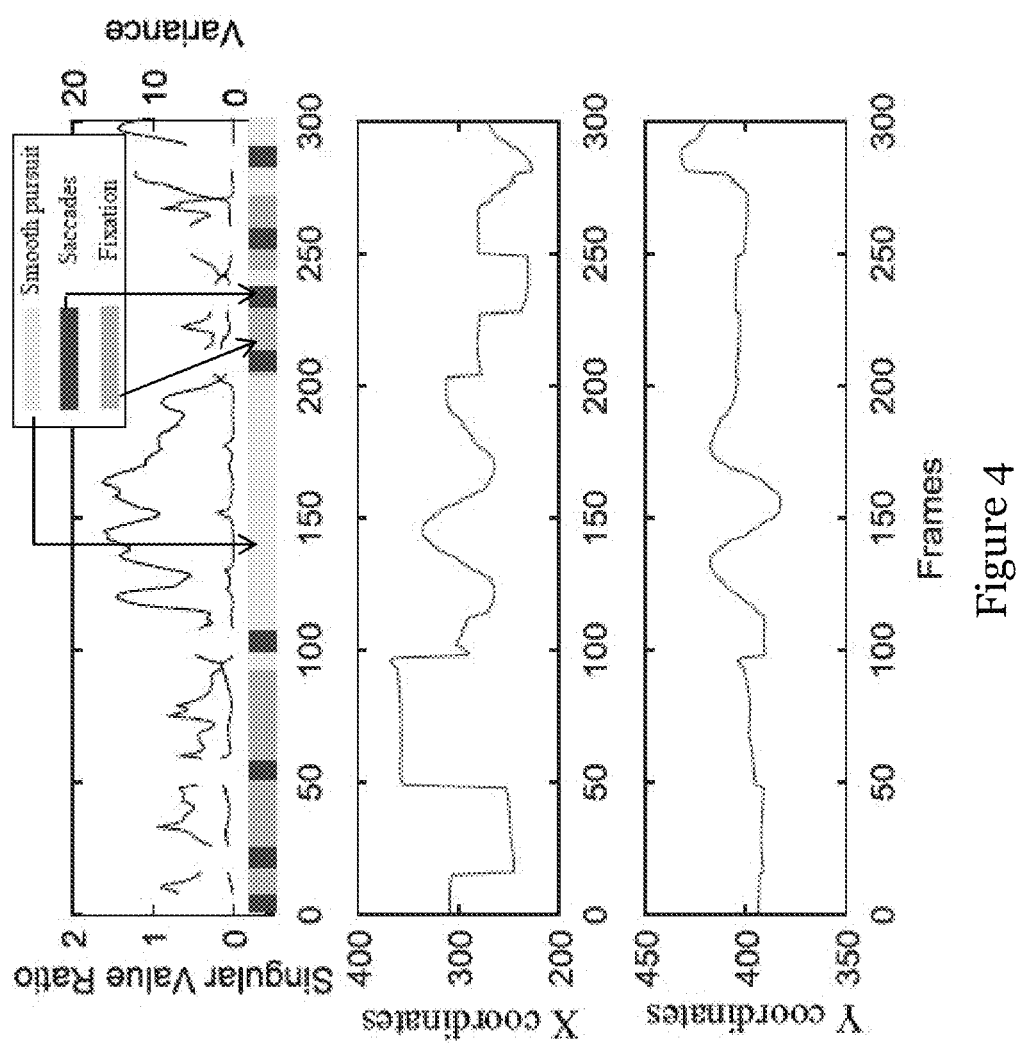
FIG. 4 shows the plot for differentiating the 3 different kinds of eye movements of FIG. 3A.

FIG. 4 shows the identification of the 3 different kinds of eye movements based on the eye movement signals detected.

In one example, an outlier removal process is performed. After the outlier removal process, both 2D PORs and pupil centers are centered on their respective means and rotated to align principal axes with X- and Y-axes. Then isometric scaling is performed such that all the pupil centers and 2D PORs lie within [−1 . . . 1] area.

B. Cross-Validated Partition of Input Space

By performing calibration at the depth $D_1$, M reliable training pairs of $\mathcal{P} = \{\mathcal{X}(p^{(i)})\}_{i=1}^M$ and $\mathcal{Y} = \{y^{(i)}\}_{i=1}^M$ are collected. Given the $n^{th}$ sub-region $\mathcal{R}_{(n)}$, $B_{(n)} = [B_{(n)}^x; B_{(n)}^y]^T$ can be resolved as a least square solution as follows $$B_{(n)} = (\mathcal{P}_{(n)} \mathcal{P}_{(n)}^T)^{-1} \mathcal{P}_{(n)} \mathcal{Y}_{(n)} \quad (4)$$

where $P_{(n)}$ and $Y_{(n)}$ denote the fat matrices holding $\{p^{(i)}\}$ and $\{y^{(i)}\}$ in $R_{(n)}$. By using $\{p^{(i)}, y^{(i)}\}$ in $\{\mathcal{P}_{(n)}, \mathcal{Y}_{(n)}\}$ as the validation set and the remaining observations $\{\mathcal{P}_{(n)}^{[-i]}, \mathcal{Y}_{(n)}^{[-i]}\}$ as the training set, the LOO error can be calculated as $$\varepsilon_{LOO} = \|y^{(i)} - B_{(n)}^{[-i]} \mathcal{X}(p^{(i)})\| \quad (5)$$

where $B_{(n)}^{[-i]} = (\mathcal{P}_{(n)}^{[-i]} \mathcal{P}_{(n)}^{[-i]T})^{-1} \mathcal{P}_{(n)}^{[-i]} \mathcal{Y}_{(n)}^{[-i]}$. Based on the Sherman Morrison formula, the matrix inversion of $\mathcal{P}_{(n)}^{[-i]} \mathcal{P}_{(n)}^{[-i]T}$ can be rapidly computed as $$\left(\mathcal{P}_{(n)}^{[-i]} \mathcal{P}_{(n)}^{[-i]T}\right)^{-1} = \Delta_{(n)} + \frac{\Delta_{(n)} \mathcal{X}(p^{(i)}) \mathcal{X}(p^{(i)})^T \Delta_{(n)}}{1 + \mathcal{X}(p^{(i)})^T \Delta_{(n)} \mathcal{X}(p^{(i)})} \quad (6)$$

where $\Delta_{(n)} = (\mathcal{P}_{(n)} \mathcal{P}_{(n)}^T)^{-1}$. To prevent local region $R_{(n)}$ from indefinitely shrinking, the area of the local region $A(R_{(n)})$ is added as a penalty term into the cross validation cost $C_{LOO}$, which is defined as $$C_{LOO} = \varepsilon_{LOO} + \lambda_A \Big/ \sqrt{A(R_{(n)})}\,.$$

In the implementation, the penalty area is computed in the normalized pupil center space and $\varepsilon_{LOO}$ is converted to the angular error. Accordingly, the selected $\lambda_A$ can be appropriate for HMGT systems with different hardware setups (e.g., camera with the particular focal length and resolutions).

---

Algorithm 1: Cross-validated Input-space Partition

Input: All training pupil centers $\{p^{(i)}\}_{i=1}^M$ and 2D
    POR observations $\{y^{(i)}\}_{i=1}^M$
Output: Partition local structures $\mathcal{R}$ $\{\mathcal{R}_{(n)}\}_{n=1}^N$
Initialize: $\mathcal{R} = \{\ \}$. Select the starting point $p_s$ by
the mean-shift method.
n = 1
while True do
    $p_{in}$ ← K nearest neighbors of $p_s$
    $\hat{C} = \{\ \}$, m = 1
    while True do
        $\hat{R}_m$ ← minimal bounding box of $p_{in}$
        $\hat{E}_m$ ← leave-one-out prediction error on $\hat{R}_m$
        $\hat{C}_m = \hat{E}_m + \lambda \mathcal{A} / \sqrt{z,34; (\hat{R}\sqrt{m})}$
        $\hat{C}$.append($\hat{C}_m$), $\hat{z},33\hat{?}$ .append($\hat{R}_m$)
        if $\hat{R}_m$ covers all $\{p^{(i)}\}$ then
            m = arg min$_m$ $\{\hat{C}_m\}$
            $\mathcal{R}$.append($\hat{R}_{\overline{m}}$)
            break
        end
        $p_{new}$ ← K nearest neighbors of $R_m$
        $p_{in}$ ← $p_{in}$ ∪ $p_{new}$
        m = m + 1
    end
    if $\forall p^{(i)}$, $p^{(i)}$ is covered by $\mathcal{R}$ then
        break
    else
        $p_s$ ← the mean-shift result on $\{p^{(i)}\}$
        uncovered by $\mathcal{R}$
        n = n + 1
    end
end
Sort $\mathcal{R} = \{\mathcal{R}_{(n)}\}$ based on the area.
for k=1...N do
    Calculate $\mathcal{A}_{cover}$ as $\mathcal{R}_{(k)}$ covered by $\mathcal{R} - \mathcal{R}_{(k)}$
    if $A_{cover} > \gamma_{cmp} * \mathcal{A}(\mathcal{R}_{(k)})$ then
        delete $\mathcal{R}_{(k)}$ in $\mathcal{R}$
    end
end

---

In one embodiment, the shape of local regions is designed as simple axis-parallel rectangles. Based on the experimental evaluations, improvements cannot be achieved by using other kinds of shapes, such as rotated rectangles and ellipses. To learn the locality of each individual sub-regions, the entire input space is progressively partitioned based on Algorithm I. More specifically, the mean-shift algorithm is applied first to look for a centroid with the highest density of uncovered data points. The K nearest pupil centers of this centroid are picked out to initialize a minimal bounding box, and a group of rectangles are generated in the expansion process to fit more training points. A new sub-region is constructed as the rectangle with the minimum $C_{LOO}$. The above sub-region generation procedure iterates until all the training points have been enclosed. The population of sub-regions can be further reduced by a compaction process. The compaction process iterates on the sorted sub-regions based on their areas, and a sub-region will be discarded if other regions cover over $\gamma_{cmp}$ percent of its area. The partitioning process is visually illustrated in FIGS. 5A to 5D.

Since the test pupil center p may lie in the overlapping area of multiple sub-regions, the matching model is selected as the one with the minimal $C_{LOO}$. Besides, if the test point p is not located in any constructed sub-regions, a local model with the closest distance to p is used as the gaze predictor.

C. Recover 2D Epipolar Point

By fitting training data at the depth $D_1$, a homogeneous mapping could be inferred as a 2D POR predictor if users are testing at $D_1$. When pupil centers $\{p^{(i)}\}_{i=1}^{M}$ are captured by gazing at points at $D_2$, parallax errors can be calculated as discrepancies between the observed 2D PORs $\{y^{(i)}\}_{i=1}^{M}$ and the virtual ones predicted by $|\{h(p^{(i)})\}_{i=1}^{M}$ (as shown in FIG. 2). An epipolar line $l_{ep}^{(i)}$ corresponding to $p^{(i)}$ can be determined as the image line connecting $y^{(i)}$ and $h(p^{(i)})$, which is given by $$l_{ep}^{(i)} = \frac{[\ y^{(i)}\ 1\ ] \otimes [\ h(p^{(i)})\ 1\ ]}{\|[\ y^{(i)}\ 1\ ] \otimes [\ h(p^{(i)})\ 1\ ]\|} \tag{7}$$

where $\Box$ denotes the cross product of two vectors. Simultaneously, since all the visual axes originate from the eyeball center, the epipolar lines theoretically intersect at the same epipolar point $[e_x\ e_y]^T$, i.e., the image point of the eyeball center. Thus, $[e_x\ e_y]^T$ can be estimated as the minimal least square solution of Equation (8), which is given by $$[e_x, e_y, 1] \mathcal{L}_{ep} = 0 \tag{8}$$

where $L_{ep}$ is a matrix holding all epipolar lines $\{l_{ep}^{(i)}\}_{i=1}^{M}$.

D. Learn 3D Gaze Model Parameters

The problem of 3D gaze model learning can be interpreted as estimation of the eyeball center position and the back projection matrices $A_{(n)} = [A^x_{(n)}\ A^y_{(n)}]$ for the local region $R_{(n)}$. To this end, a nonlinear optimization problem is formulated to minimize the angular distances between the observed gaze directions $\{(G_{3D}^{(i)} - e)\}_{i=1}^{M+\tilde{M}}$ and the predicted ones $\{d(p^{(i)})\}_{i=1}^{M+\tilde{M}}$, which is given as $$\min_{e,\{A_{(n)}\}} \sum_{n=1}^{N} \sum_{p^{(i)} \in R_{(n)}} \frac{\|d(p^{(i)}) \otimes (\mathcal{P}_{3D}^{(i)} - e)\|}{\|d(p^{(i)})\| \|\mathcal{P}_{3D}^{(i)} - e\|} \tag{9}$$

subject to $e \in \eta_{cstr}$, where $\eta_{cstr}$ denotes the feasible range of the eye position, $\{P_{3D}^{(i)}\}_{i=1}^{M+\tilde{M}}$ are the 3D coordinates of PORs at $D_1$ and $D_2$, which can be achieved by a Perspective-n-Point algorithm. Here, it is necessary to incorporate the constraint $e \in \eta_{cstr}$ in Equation (9). Otherwise, eye positions far away from the scene camera, i.e. $\|e\| \to \infty$, are likely to be learned as the trivial solutions of Equation (9), in which cases $\{d(p^{(i)})\}$ will associate with a constant gaze direction by setting coefficients of the non-constant components in Equation (1) to zeros.

For addressing the nonlinear optimization problem like Equation (9), it is paramount to initialize the parameters with reasonable values. In this embodiment, the following initialization strategy is adopted. The position of the eyeball center with respect to the scene camera can be presented as $\lambda_e K_{cam}^{-1} [e_x, e_y, 1]^T$, where $K_{cam}$ is the intrinsic matrix of the scene camera and $\lambda_e$ is the distance between the eyeball center and the scene camera. Thus, the eyeball position $e_{init}$ can be initialized as $\lambda_{init} K_{cam}^{-1} [e_x, e_y, 1]^T$, where $\lambda_{init}$ denotes the rough displacement estimation considering the physical structure of HMGT. Accordingly, $A^x_{(n)}$ and $A^y_{(n)}$ of the $n^{th}$ sub-model can be initialized by minimizing algebraic errors as follows $$A^x_{(n)} = \operatorname{argmin} \sum_{p^{(i)} \in R_{(n)}} \left\| A^x_{(n)} \mathcal{X}(p^{(i)}) - \frac{\mathcal{P}_{3Dx}^{(i)} - e_{initx}}{\mathcal{P}_{3Dz}^{(i)} - e_{initz}} \right\| \tag{10}$$

$$A^y_{(n)} = \operatorname{argmin} \sum_{p^{(i)} \in R_{(n)}} \left\| A^y_{(n)} \mathcal{X}(p^{(i)}) - \frac{\mathcal{P}_{3Dy}^{(i)} - e_{inity}}{\mathcal{P}_{3Dz}^{(i)} - e_{initz}} \right\|$$

where $\mathcal{P}_{3Dx}^{(i)}$, $\mathcal{P}_{3Dy}^{(i)}$ and $\mathcal{P}_{3Dz}^{(i)}$ are the X-, Y- and Z-coordinates of $\mathcal{P}_{3D}^{(i)}$ respectively. A linear closed-form solution for Equation (10) can be easily obtained.

In practical implementation, it has been observed that the optimization problem of Equation (9) involves a large number of optimization variables thereby resulting in a heavy computational cost. Meanwhile, Equation (9) can be expressed as a bi-level optimization problem as follows $$\min \zeta(e), e \in \eta_{cstr} \tag{11}$$

where the function $\zeta(e)$ is given by $$\zeta(e) = \min_{\{A_{(n)}\}} \sum_{n=1}^{N} \sum_{p^{(i)} \in R_{(n)}} \frac{\|d(p^{(i)}) \otimes (\mathcal{P}_{3D}^{(i)} - e)\|}{\|d(p^{(i)})\| \|\mathcal{P}_{3D}^{(i)} - e\|}. \tag{12}$$

In other words, the 3D model learning process can be described as looking for the eye position e with the minimum $\zeta(e)$. Here define $\zeta(e)$ as the angular inconsistency in fitting 3D PORs at two different depths, which is caused by assigning the incorrect eye position. Specifically, two closely-located pupil centers correspond to the similar gaze directions if the accurate eye position ê can be learned (as shown in FIG. 6A). When the eye position is imprecisely estimated as $\tilde{e} = \hat{e} + \Delta e$, the directions calculated by $P_{3d}^{(i)} - \tilde{e}$ will also show a tiny change when these two visual axes directed at points with the same depth. However, a sharp variation occurs when gaze points are located at the different depths (as shown in FIG. 6A). In other words, a small change in pupil center positions is likely to render both slight and noticeable variations in gaze directions. Consequently, the surface created by $\{p^{(i)}, (d_x^{(i)}, d_y^{(i)})\}_{i=1}^{M+\tilde{M}}|_{e=\tilde{e}}$ appears much rougher than the one computed by the correct eye position $\tilde{e}$ (as shown in FIGS. 6B and 6C). The polynomial regression d(q) is unable to characterize this kind of "roughness", which leads to the structured fitting residual $\zeta(\tilde{e})$.

Large computational resources are required for solving the bi-level optimization of Equation (11) since the lower-level problem. Equation (12) belongs to the fractional optimization problem without trivial solutions. Based on the experimental observations, only a slight disparity in prediction results will arise when $\{A_{(n)}\}$ inferred by minimizing Equation (12) is approximated by the closed form solution of Equation (10). Hence, in one embodiment, Equation (11) can be modified as $$\min_{e,\{A_{(n)}\}} \sum_{n=1}^{N} \sum_{p^{(i)} \in R_{(n)}} \frac{\|d(p^{(i)}) \otimes (\mathcal{P}_{3D}^{(i)} - e)\|}{\|d(p^{(i)})\| \|\mathcal{P}_{3D}^{(i)} - e\|}, \tag{13}$$

-continued s.t. $e \in \eta_{estr}$ $A_{(n)}^x = \Psi_{(n)}^x(e)$ $A_{(n)}^y = \Psi_{(n)}^y(e)$ $d(p^{(i)}) = \begin{bmatrix} A_{(n)}^x \mathcal{X}(p^{(i)}) \\ A_{(n)}^y \mathcal{X}(p^{(i)}) \\ 1 \end{bmatrix}$ where $\Psi_{(n)}^x$ and $\Psi_{(n)}^y$ are the analytical solutions of Equation (10). Consequently, Equation (11) can be further reduced to an optimization problem only with variables $e=[e_x,e_y,e_z]^T$. This significantly scales down computing complexity hence speeds up the optimization process.

III. Impacts of Calibration Depths on Model Learning Results

One key aspect of the present embodiment concerns careful selection of calibration depths. In some applications, one calibration depth is insufficient to recover 2D and 3D gaze models. Additionally or alternatively, in some applications, more than two calibration depths will not benefit the model learning results if without proper placements. In this embodiment of the invention, two calibration depths based on the difference of their reciprocals, i.e., $1/D_1-1/D_2$ are applied.

Figure 7:
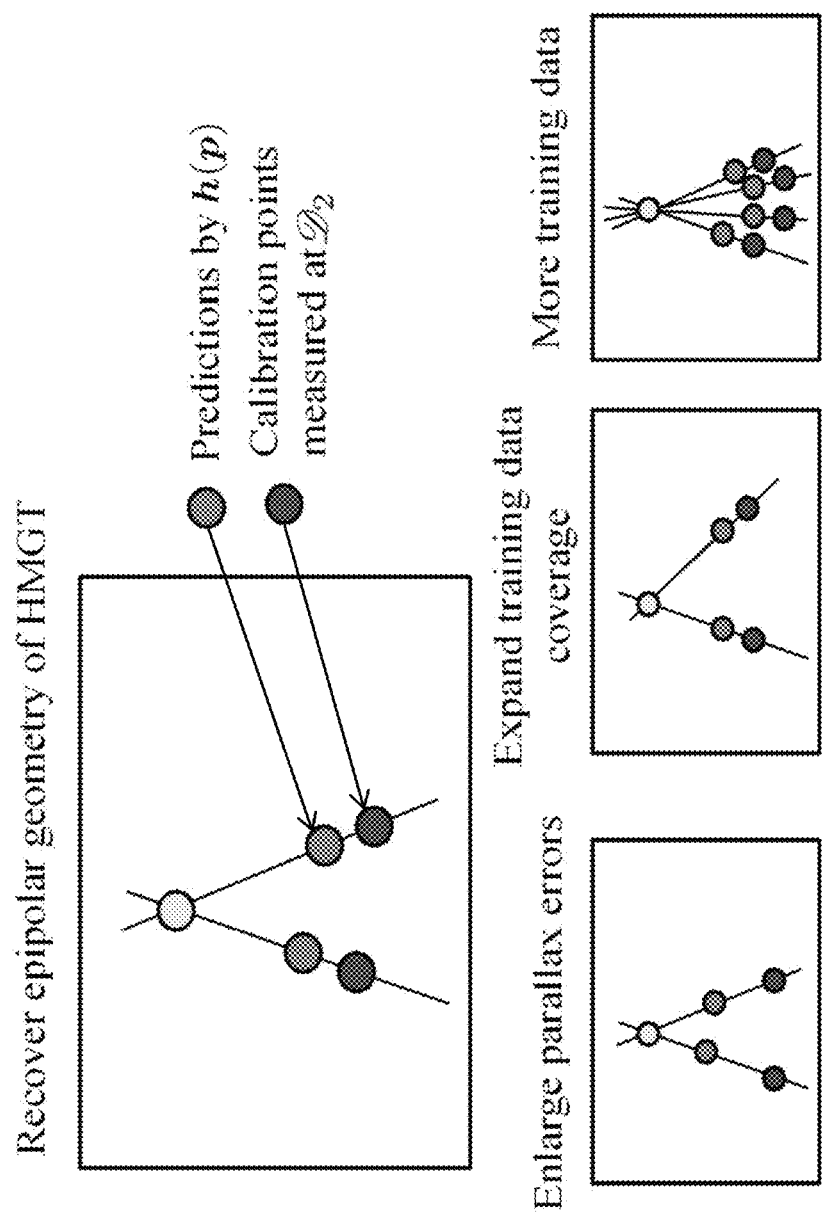
FIG. 7 are diagrams illustrating the factors influencing the epipolar recovery accuracy.
Figure 8:
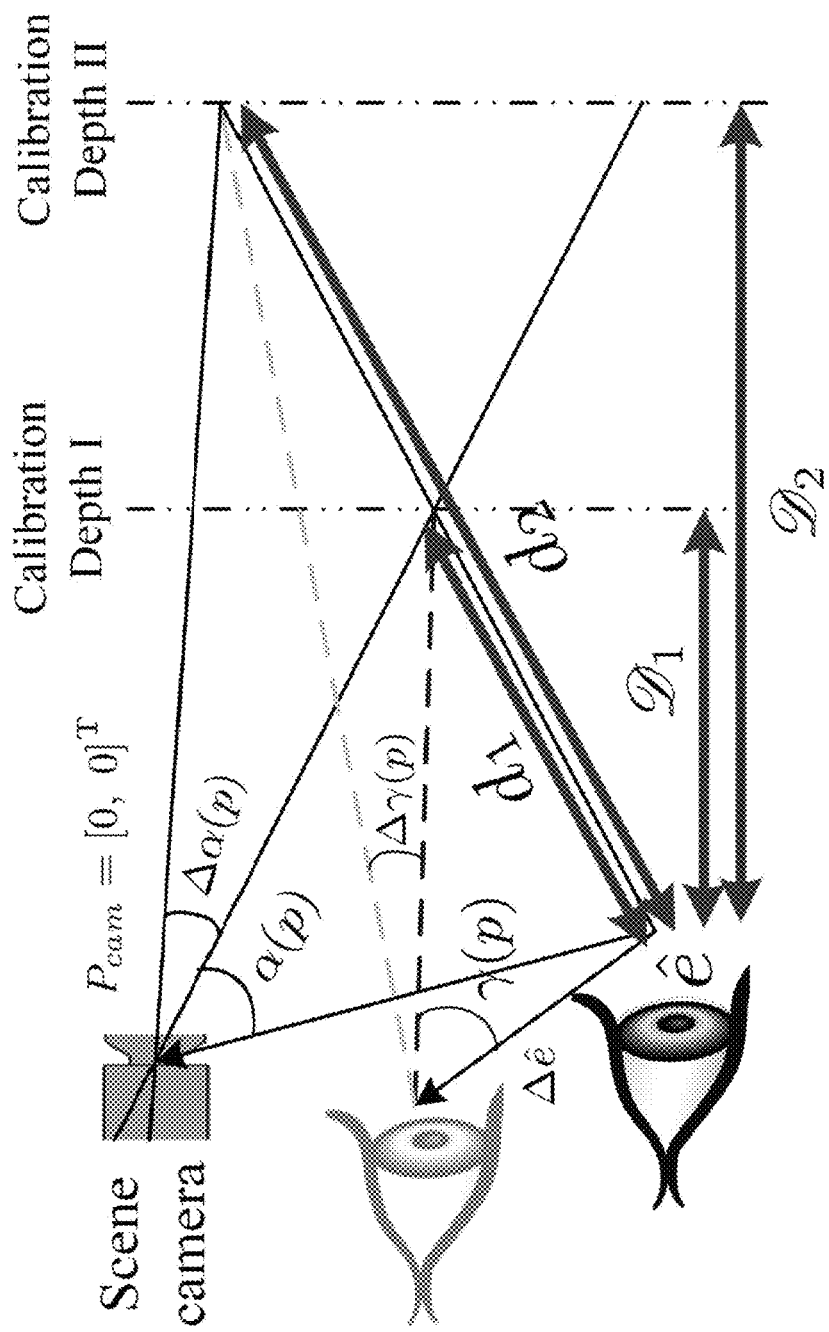
FIG. 8 is a diagram illustrating the parallax error and structured angular inconsistency in the model.

As shown in FIG. 7, there are three primary approaches to improve the accuracy of epipolar point estimation: (1) expanding the training data coverage, (2) collecting more training data and (3) increasing parallax errors measured at $D_2$. The first two approaches can be implemented by increasing the head rotation range and extending the calibration period. The third approach depends on the proper selection of calibration depths. As shown in FIG. 8, when the user is gazing a point at depth of $D_2$, the projection of m will be predicted by h(p), which gives rise to the parallax angular error $\Delta\alpha(p)$. Considering the geometrical relationship in FIG. 8, it can be derived that $\Delta\alpha(p)$ is linearly proportional to $1/D_1-1/D_2$. Thus, an increase in $1/D_1-1/D_2$ can result in a larger parallax error, thereby benefiting the epipolar structure recovery of HMGT systems.

The selection of calibration depths also affects the accuracy of eye position estimation in the 3D prediction model by adjusting the sensitiveness of $\zeta(\hat{e}+\Delta e)$ with respect to $\Delta e$. To analyze the relationship between calibration depths and $\zeta(\hat{e})$, it is assumed that $Pr(p|D=D_1)=Pr(p|D=D_2)$, where $Pr(p|D)$ denotes possibility of observing the pupil center p at the depth D. The expectation of $\zeta(\hat{e})$ can be obtained as $$E(\zeta(\hat{e})) = \int \frac{\|d(p) \otimes (\hat{\mathcal{P}}(p, \mathscr{D}_1) - \hat{e})\|}{\|d(p)\| \|\hat{\mathcal{P}}(p, \mathscr{D}_1) - \hat{e}\|} Pr(p | \mathscr{D} = \mathscr{D}_1) dp + \int \frac{\|d(p) \otimes (\hat{\mathcal{P}}(p, \mathscr{D}_2) - \hat{e})\|}{\|d(p)\| \|\hat{\mathcal{P}}(p, \mathscr{D}_2) - \hat{e}\|} Pr(p | \mathscr{D} = \mathscr{D}_2) dp \quad (14)$$

where $\hat{\mathcal{P}}(p, \mathscr{D})$ denotes the 3-D intersection point between the visual axis associating with p and the calibration surface at the depth D. Meanwhile:

$$\frac{\|d(p) \otimes (\hat{\mathcal{P}}(p, \mathscr{D}_1) - \hat{e})\|}{\|d(p)\| \|\hat{\mathcal{P}}(p, \mathscr{D}_1) - \hat{e}\|} + \frac{\|d(p) \otimes (\hat{\mathcal{P}}(p, \mathscr{D}_2) - \hat{e})\|}{\|d(p)\| \|\hat{\mathcal{P}}(p, \mathscr{D}_2) - \hat{e}\|} \geq \frac{\|(\hat{\mathcal{P}}(p, \mathscr{D}_1) - \hat{e}) \otimes (\hat{\mathcal{P}}(p, \mathscr{D}_2) - \hat{e})\|}{\|(\hat{\mathcal{P}}(p, \mathscr{D}_1) - \hat{e})\| \|(\hat{\mathcal{P}}(p, \mathscr{D}_2) - \hat{e})\|}. \quad (15)$$

The equality of Equation (15) will hold when $\|d(p) \otimes (\hat{\mathcal{P}}(p, \mathscr{D}_1) - \hat{e})\|=0$ or $\|d(p) \otimes (\hat{\mathcal{P}}(p, \mathscr{D}_2) - \hat{e})\|=0$. That is to say, d(p) can precisely predict directions of $(\hat{\mathcal{P}}(p, \mathscr{D})-e)$ at a single depth. As shown in FIG. 8 the intersection angle between $(\hat{\mathcal{P}}(p, \mathscr{D}_1)-e)$ and $(\hat{\mathcal{P}}(p, \mathscr{D}_2)-e)$ is linearly proportion to $|\Delta e|\sin(\gamma(p))(1/\mathscr{D}_1-1/\mathscr{D}_2)$. Thus, $$E(\zeta(\hat{e})) \geq \tau |\Delta e|(1/\mathscr{D}_1-1/\mathscr{D}_2) \int \sin(\gamma(p)) Pr(p) dp \quad (16)$$

where $\tau$ is a constant value.

Figure 9:
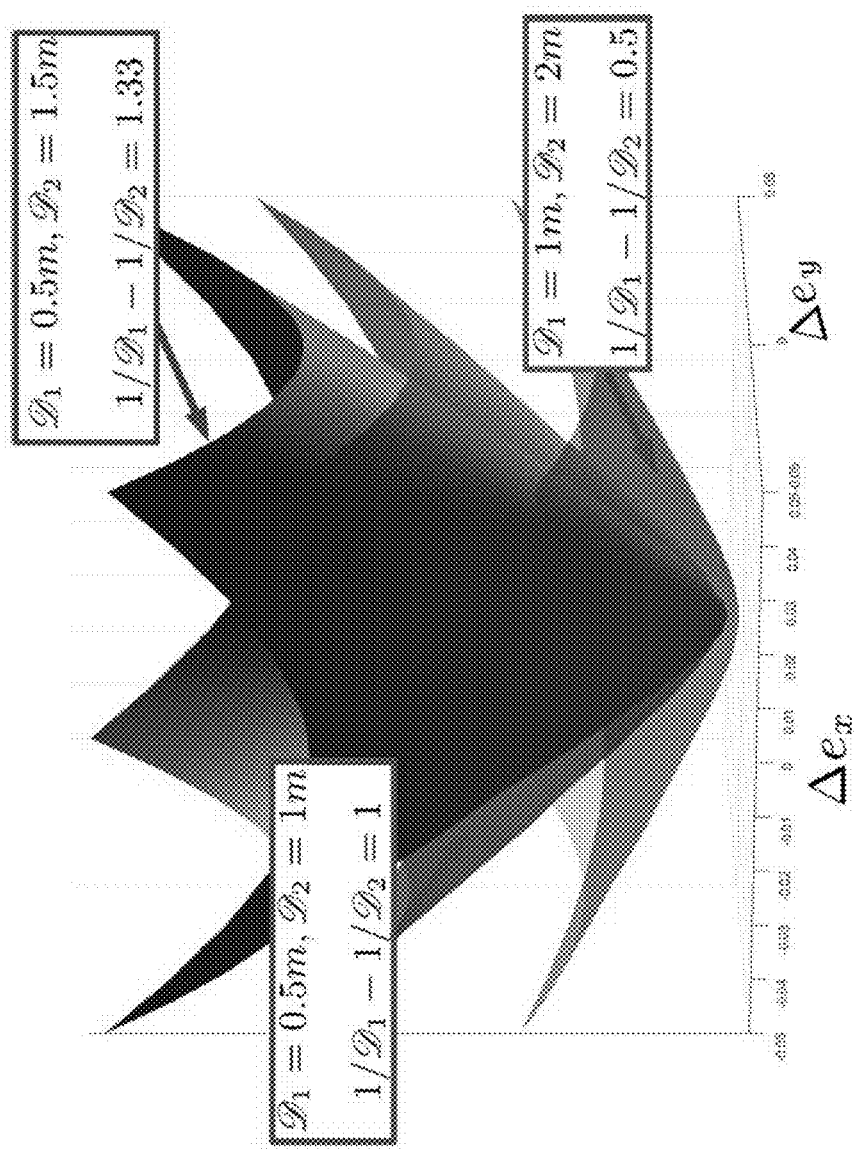
FIG. 9 shows the relation between $\Delta e$ and $\varepsilon(\hat{e}+\Delta e)$ when considering different combinations of the two calibration depths $D_1$ and $D_2$.

Based on Equation (16), it can be determined that $E(\zeta(\hat{e}))$ is linearly proportional to $(1/D_1-1/D_2)$. Based on the fully controlled gaze simulation environment developed, the relation between $\Delta e$ and $\zeta(\hat{e}+\Delta e)$ is drawn in FIG. 9 by using three different combinations of calibration depths. By comparing the depth pairs $\{D_1=1\text{ m}, D_2=2\text{ m}\}$ and $\{D_1=0.5\text{ m}, D_2=1\text{ m}\}$, the later combination has a smaller depth discrepancy but renders $\mathcal{E}(\hat{e}+\Delta e)$ more sensitive to $|\Delta e|$ by introducing a larger $(1/D_1-1/D_2)$. The problem of finding the optimal $\hat{e}$ typically shows more robustness to numerical accuracy and observation noises when the region around e become more curved. Thus, a better estimation on e can be achieved by increasing $(1/D_1-1/D_2)$.

Figure 10A:
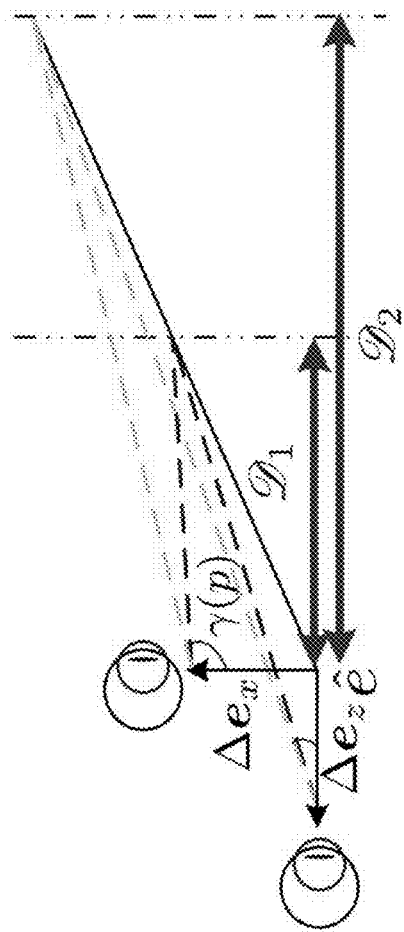
FIG. 10A shows a geometric plot illustrating the impacts of $\Delta e_x$ and $\Delta e_z$ on $\varepsilon(\hat{e}+\Delta e)$.
Figure 10B:
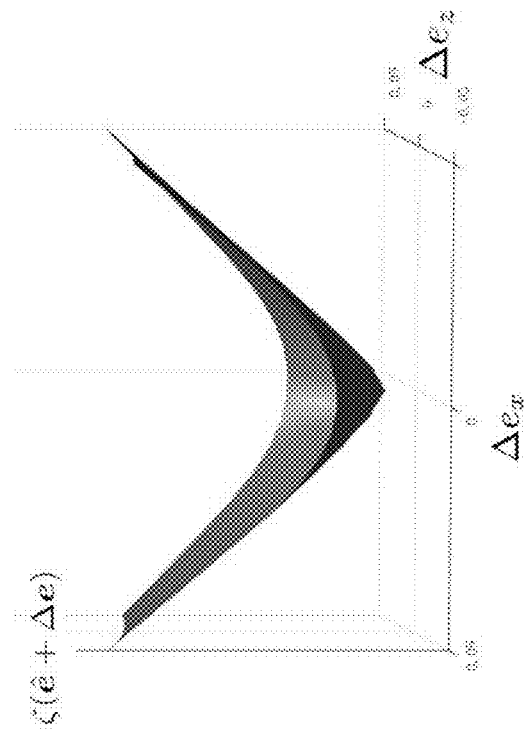
FIG. 10B shows a graph illustrating the impacts of $\Delta e_x$ and $\Delta e_z$ on $\varepsilon(\hat{e}+\Delta e)$.
Figure 11:
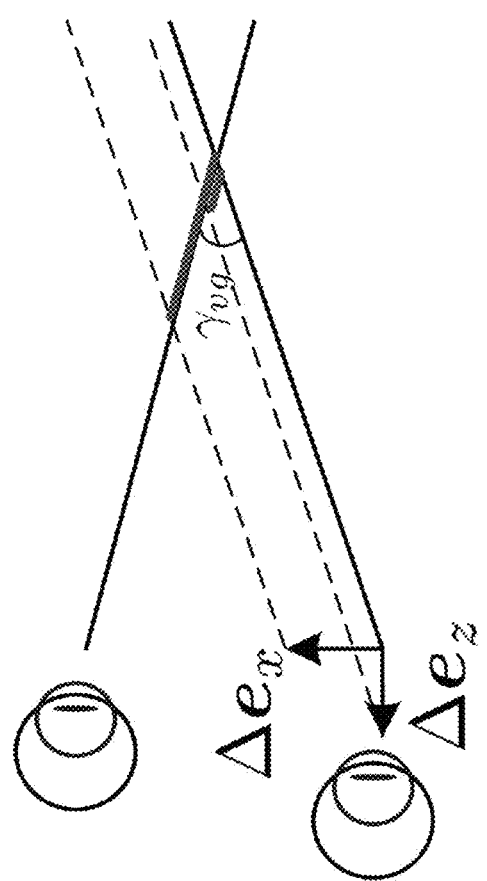
FIG. 11 shows a geometric plot illustrating the impacts of $\Delta e_x$ and $\Delta e_z$ on 3D gaze prediction.
Figure 12:
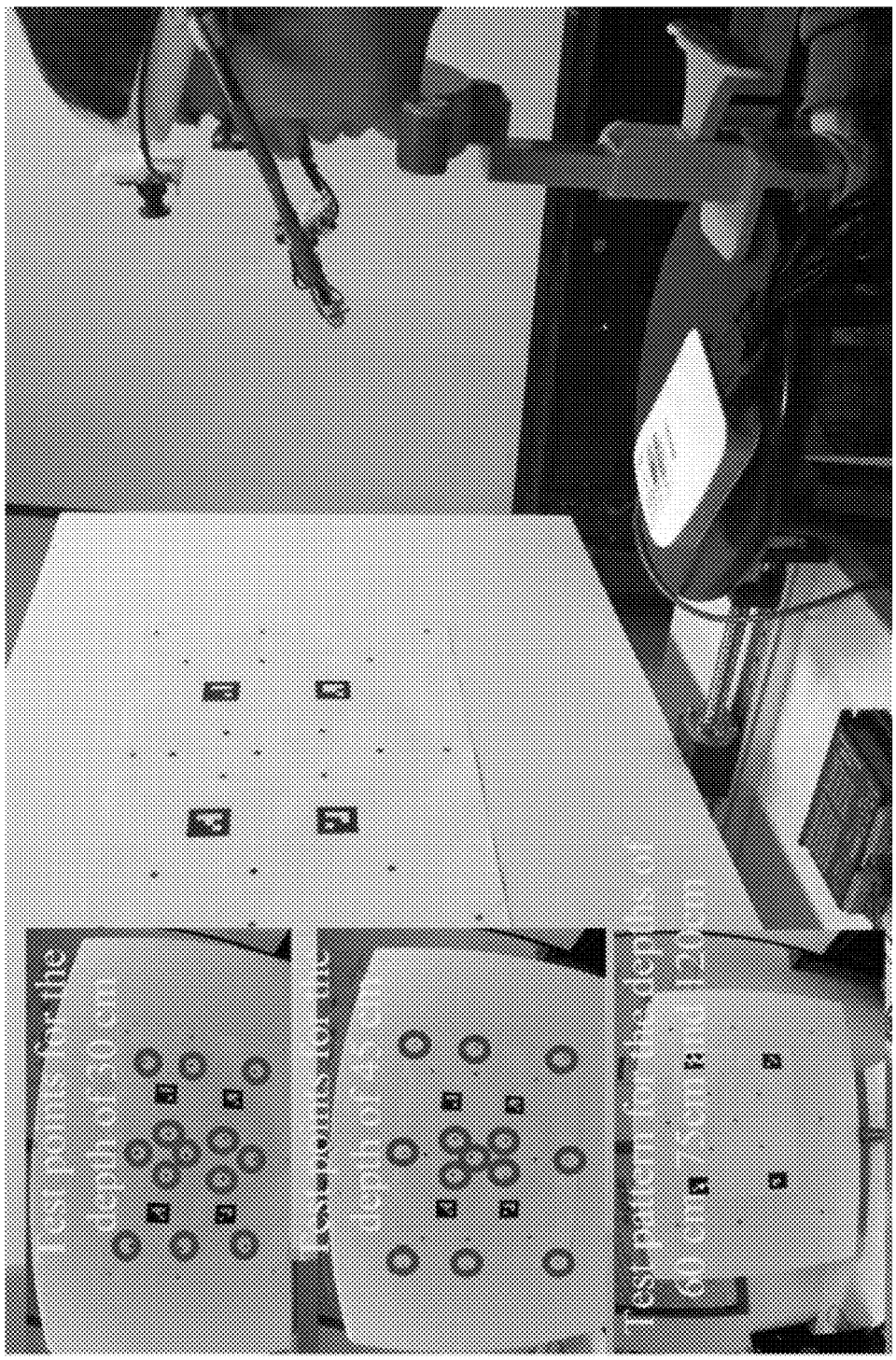
FIG. 12 is a picture showing the test setup for evaluating 3D POR estimation precision with different test patterns.

Additionally, it can be noted that $E(\zeta(\hat{e})) \to 0$ if $\int \sin(\gamma(p)) Pr(p) dp \to 0$. This situation will occur when most gaze directions are enveloped within a small direction range, and $\Delta e$ also lies in this range. In this regard, a wide angle range of head-rotation motion can not only reduce the extrapolation risk in cases of large viewing fields but also aid the better estimation on eye positions. Meanwhile, when $\Delta e$ moves along X- and Y-axes, it will correspond to a larger $\gamma(p)$ than the shift along the Z-axis (as shown in FIG. 10A). Accordingly, $E(\zeta(\hat{e}))$ is less sensitive to the variation along the Z-axis (as shown in FIG. 10B), which accounts for difficulties in precisely inferring the depth information of eyeball centers. Fortunately, considering the small vergence angle $\gamma_{vg}$ of two visual axes, $\Delta e_z$ is less likely to propagate notable triangulation errors than $\Delta e_x$ (as shown in FIG. 11).

Under conditions of the real PnP observation noises, the local minimal position of $\zeta(\hat{e})$ may significantly move back along the Z-direction or even disappear since $\zeta(\hat{e})$ typically shows a small gradient in the Z-direction and a larger eye position depth is more likely to mitigate the influence of PnP observation noises. Thus, the optimization will probably end with an eye position close to the minimal depth of the pre-defined constraint. Following this concern, it is a safe operation to design the constraint with a narrow feasible range along the Z-axis. In contrast, a comparably broad feasible area can be allowed in the X- and Y-axes since the eye positions in these two directions can be well estimated by solving Equation (13) and are more important to 3D gaze prediction.

IV. Experimental Results

To corroborate the method of the present embodiment, a low cost HMGT has been developed. Two 25 fps eye cameras are with resolutions of 640×512 pixels. To mitigate the motion blur during the head-rotation motion, a global shutter wide angle camera is used as the scene image sensor, which has the resolution of 1280×720 pixels and is calibrated by OpenCV library. Six subjects take part in the experiment. Three of them are nearsighted and wearing corrective contact lenses, ranging from 2 to 5 diopters. To evaluate effects of calibration depths on prediction results, training gaze data are collected at three different depths, i.e., $d_1=0.45\sim0.5$ m, $d_2=0.9$ m$\sim$1 m and $d_3=1.4$ m$\sim$1.5 m, respectively. And the calibration at each depth lasts for 25 seconds. The test procedure consists of asking subjects to look at specific points on the panel at five depths, ranging from 0.3 to 1.2 m. The viewing angle range remains almost the same for test depths of 0.3 m, 0.45 m and 0.6 m, with about 15° and 20° in the vertical ascending and descending directions, 25° in the left and right directions. For the test depths of 0.6 m, 0.75 m and 1.2 m, the test pattern with the same physical size is used. All subjects repeat the entire calibration and test procedure three times. Given the certain test depth, the mean of each repetition is presented as the error metrics.

Figure 13A:
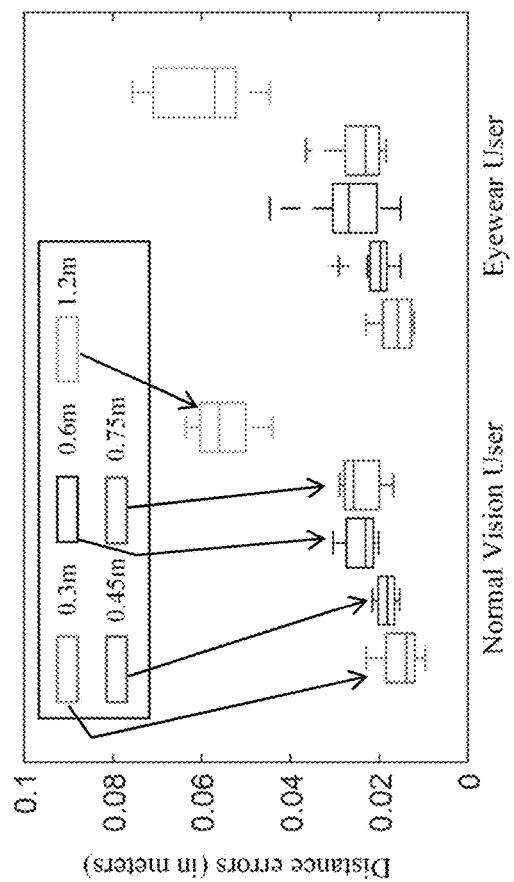
FIG. 13A is a graph showing prediction errors in the Z-direction with test depths of 0.3 m, 0.45 m, 0.6 m, 0.75 m, and 1.2 m.
Figure 13B:
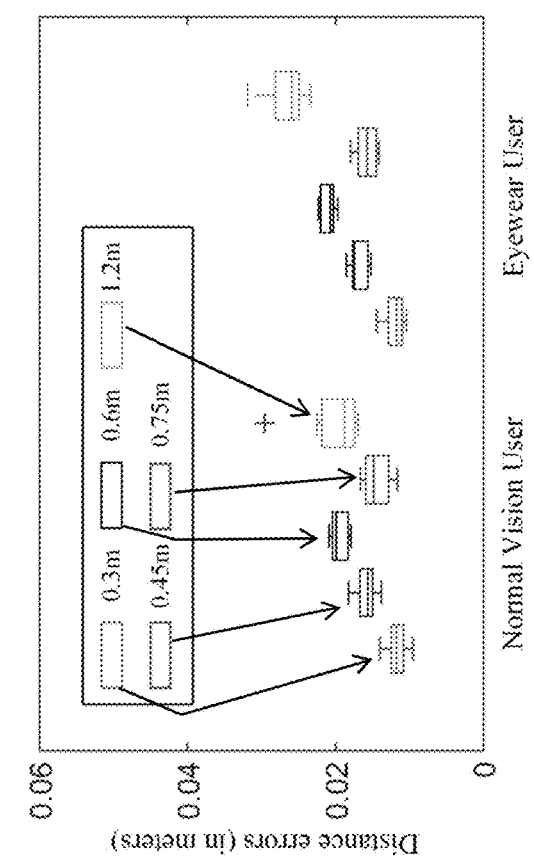
FIG. 13B is a graph showing prediction errors in the X-Y plane with test depths of 0.3 m, 0.45 m, 0.6 m, 0.75 m, and 1.2 m.
Figure 13C:
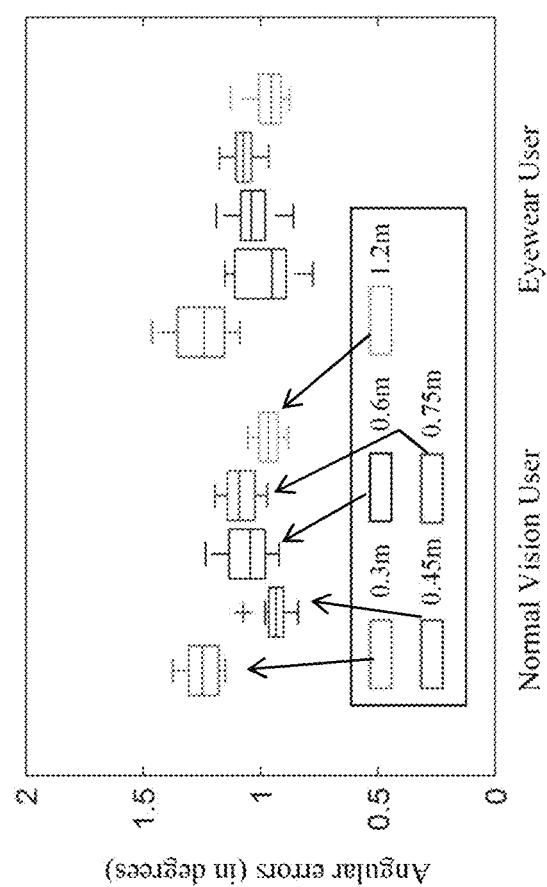
FIG. 13C is a graph showing prediction errors in 2D gaze estimation with test depths of 0.3 m, 0.45 m, 0.6 m, 0.75 m, and 1.2 m.

FIGS. 13A to 13C are graphs showing prediction errors in the Z-direction (depth errors), in the X-Y plane (facing errors), and in the 2D gaze estimation, for normal vision users and eyewear users In this example, at first, gaze data at 0.5 m and 1.5 m are used as training data for the gaze predictor of the present embodiment. As shown in FIG. 13B, the mean error in the facing plane is within 2 cm at 0.3 m$\sim$0.75 m and slightly rises beyond 2 cm at 1.2 m. From FIG. 13C, it can be seen that the method of the present embodiment can achieve consistent prediction accuracy over different test depths by successfully compensating the parallax and interpolation/extrapolation errors. Besides, it is unable to draw a conclusion that the gaze estimation performance for normal vision users outperforms that for eyewear users.

Figure 14A:
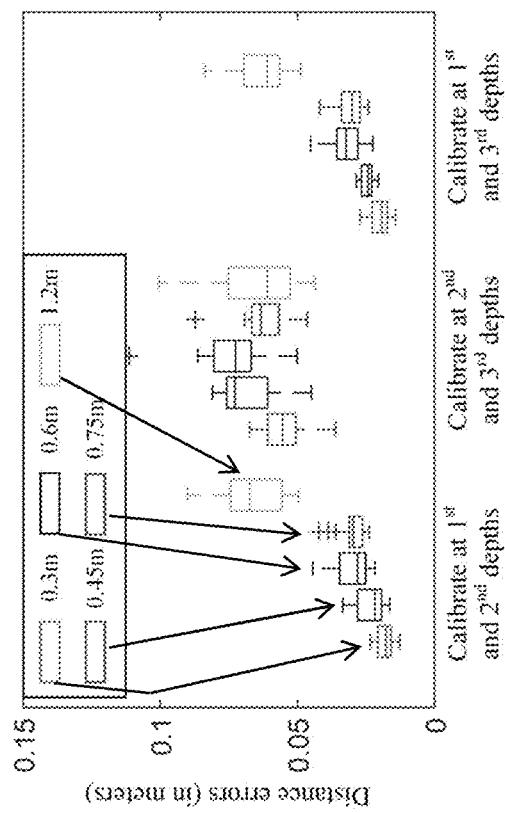
FIG. 14A is a graph showing comparison of 3D prediction errors on different combinations of depth pairs.
Figure 14B:
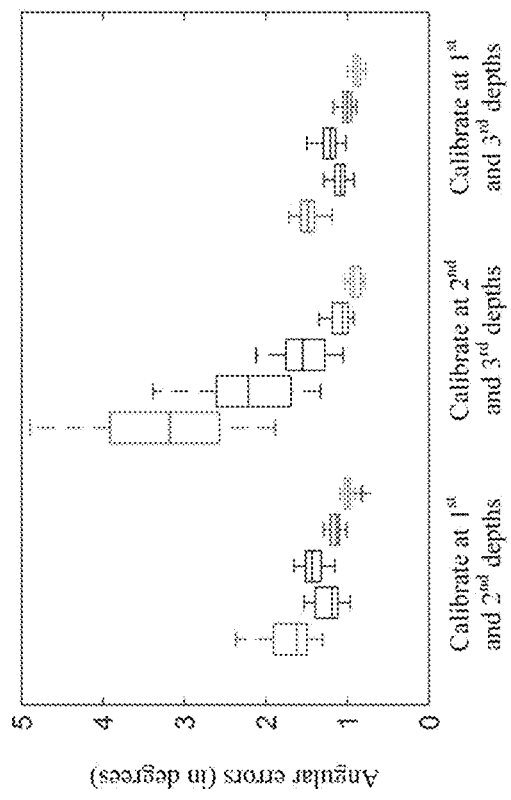
FIG. 14B is a graph showing comparison of 2D prediction errors on different combinations of depth pairs.

The effect of calibration depth selection is evaluated by choosing two depths from 0.5 m$\sim$1.5 m. FIGS. 14A and 14B are graphs showing comparison of 3D prediction errors and 2D prediction errors on different combinations of depth pairs.

As shown in FIG. 14A, the gaze predictor using 0.5 m and 1.5 m presents better accuracy in both 2D and 3D gaze estimation than those of the other two combinations. The prediction model using 1 m and 1.5 m also achieves a comparably good precision at 1.2 m primarily because this test depth lies in the interval (1 m, 1.5 m). In contrast, the prediction model using 0.5 m and 1 m not only behaves well at 0.3 m$\sim$0.75 m, but also at the extrapolation depth of 1.25 m. This better generalization ability can be attributed to the precise inference on eyeball positions via preferring a larger $(1/D_1-1/D_2)$. Compared with 3D model calibration, the suitable selection of calibration depths is also essential to the epipolar geometry recovery of HMGT systems. As shown in FIG. 14B, the 2D predictor using (0.5 m, 1.5 m) achieves the superior performance than the other two models, especially notable at 0.3 m.

V. Exemplary System

Figure 15:
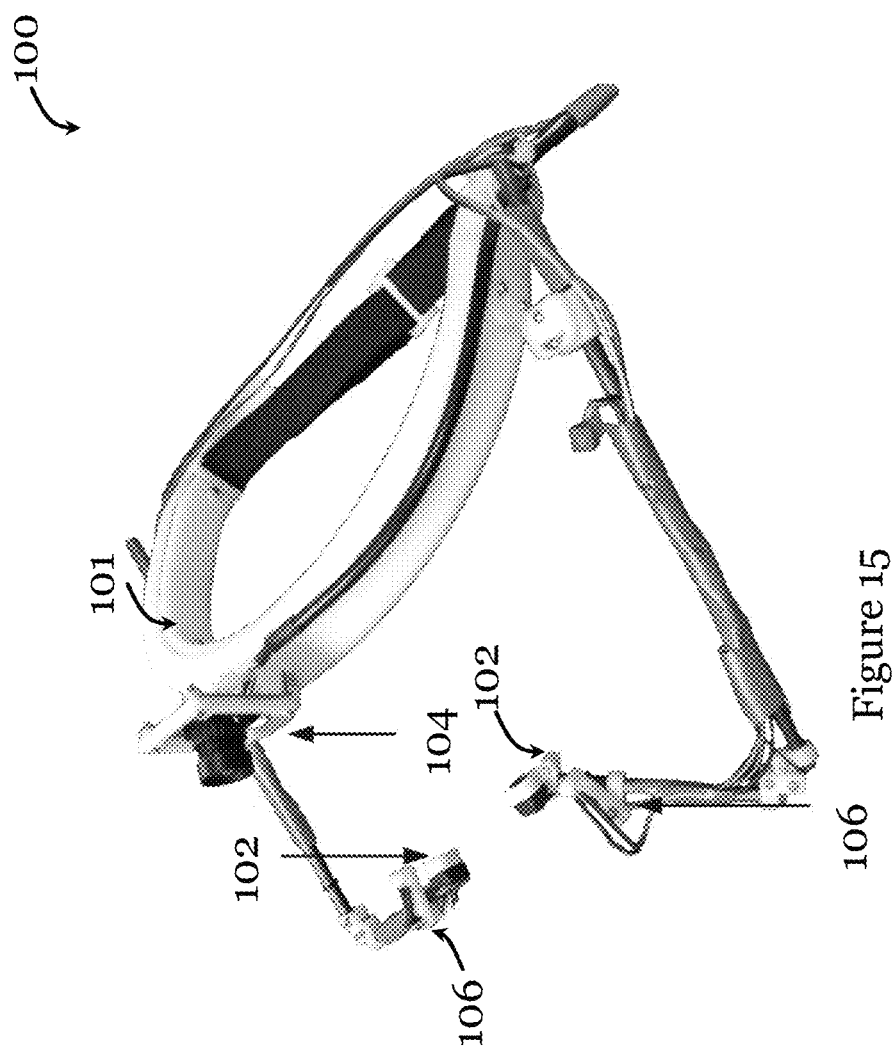
FIG. 15 is a photo of a wearable device for implementing the gaze point estimation method in one embodiment of the invention.
Figure 16:
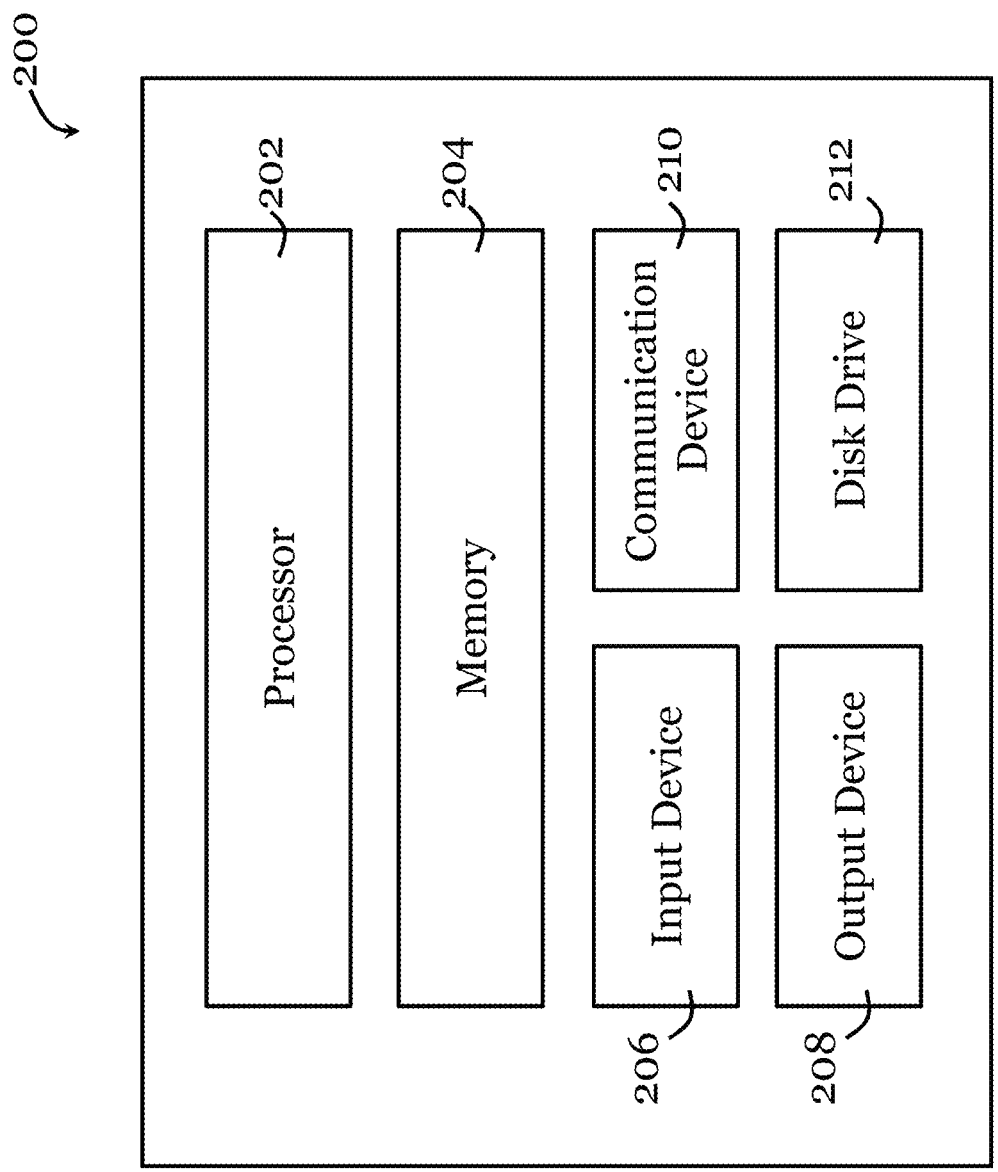
FIG. 16 is a block diagram of a system for implementing the gaze estimation method in one embodiment of the invention.

Referring to FIG. 15, there is shown a wearable device 100 for implementing the gaze point estimation method in one embodiment of the invention. The device generally includes a frame 101 that allows the user to wear the device 100 on the head. In this example, the frame 101 is made by lightweight carbon tubes and resins 3D structures made by a UV-based 3D printer. Two small 25 fps cameras 102 (1 cm×1 cm×1 cm), function as eye cameras for imaging the eyes, are mounted on the frame. A global shutter 60 fps camera 104, functioning as scene image sensor, is mounted to a loop portion of the frame. This global shutter 60 fps camera 104 mitigates the motion blur caused by the head-rotation movements. Additionally, two infrared lights 106 (wavelength 850 nm), one in respect of each eye camera 102, are mounted near the eye camera 102. The lights 106 are arranged to create the sharp contrast between the pupil and the iris, to allow the pupil centers to be precisely localized in the eye images. Power and data cables for the cameras and lights are routed corresponding around and attached to the frame 101, Referring to FIG. 16, there is shown a schematic diagram of an exemplary information handling system 200 that can be used as a server or other information processing systems for performing at least part of the gaze estimation method (above-described) in one embodiment of the invention. The information handling system 200 may have different configurations, and it generally comprises suitable components necessary to receive, store, and execute appropriate computer instructions, commands, or codes. The main components of the information handling system 200 are a processor 202 and a memory unit 204. The processor 202 may be formed by one or more CPU, MCU, controllers, logic circuits, Raspberry Pi chip, etc. The memory unit 204 may include one or more volatile memory unit (such as RAM, DRAM, SRAM), one or more non-volatile unit (such as ROM, PROM, EPROM, EEPROM, FRAM, MRAM, FLASH, SSD, NAND, and NVDIMM), or any of their combinations. Preferably, the information handling system 200 further includes one or more input devices 206 such as a keyboard, a mouse, a stylus, an image scanner, a microphone, a tactile input device (e.g., touch sensitive screen), and an image/video input device (e.g., camera). The information handling system 200 may further include one or more output devices 208 such as one or more displays (e.g., monitor), speakers, disk drives, headphones, earphones, printers, 3D printers, etc. The display may include a LCD display, a LED/OLED display, or any other suitable display that may or may not be touch sensitive. The information handling system 200 may further include one or more disk drives 212 which may encompass solid state drives, hard disk drives, optical drives, flash drives, and/or magnetic tape drives. A suitable operating system may be installed in the information handling system 200, e.g., on the disk drive 212 or in the memory unit 204. The memory unit 204 and the disk drive 212 may be operated by the processor 202. The information handling system 200 also preferably includes a communication device 210 for establishing one or more communication links (not shown) with one or more other computing devices such as servers, personal computers, terminals, tablets, phones, or other wireless or handheld computing devices. The communication device 210 may be a modem, a Network Interface Card (NIC), an integrated network interface, a radio frequency transceiver, an optical port, an infrared port, a USB connection, or other wired or wireless communication interfaces. The communication links may be wired or wireless for communicating commands, instructions, information and/or data. Preferably, the processor 202, the memory unit 204, and optionally the input devices 206, the output devices 208, the communication device 210 and the disk drives 212 are connected with each other through a bus, a Peripheral Component Interconnect (PCI) such as PCI Express, a Universal Serial Bus (USB), an optical bus, or other like bus structure. In one embodiment, some of these components may be connected through a network such as the Internet or a cloud computing network. A person skilled in the art would appreciate that the information handling system 200 shown in FIG. 16 is merely exemplary and different information handling Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the invention are either wholly implemented by computing system or partly implemented by computing systems then any appropriate computing system architecture may be utilized. This will include stand-alone computers, network computers, dedicated or non-dedicated hardware devices. Where the terms "computing system" and "computing device" are used, these terms are intended to include any appropriate arrangement of computer or information processing hardware capable of implementing the function described.

Embodiments of the invention has provided a region-wise learning model for 2D and 3D POR estimation with mobile gaze trackers. The learning model is motivated from an idea that the input space of pupil centers can be clustered into a set of sub-regions such that simple local models suffice to fit the training data in each sub-region. For each local model, an epipolar line and a visual axis should be predicted given a pupil center, thus 2D and 3D PORs can be calculated as the intersection point of two epipolar lines and visual axes, respectively. A local homography-like relation can be learned at first for fitting one-depth gaze data, which allows the fast computation of the Leave-One-Out (LOO) errors. Accordingly, the partitioning structure can be determined in a cross-validated manner. Then, the parallax errors observed at another calibrated depth are leveraged to restore the epipolar point position. Correspondingly, a point to line relationship can be easily inferred based on the epipolar point and homography-like mapping. Due to adoption of the same local projection approximation, the 3D model shares the same space partitioning structure as the 2D correspondence. Then, a constrained nonlinear optimization problem is formulated to derive the 3D eyeball center and back-projection mapping for each region. Given the epipolar point in the 2D model, the nonlinear optimization is initialized with the rough estimation of the eyeball center. Depending on the optimization results, the visual axes of both eyes can be estimated from the suitable local model, and the 3D gaze point can be inferred as the point closest to two visual axes. To aid the practical implementation, a sensible constraint for eyeball positions can be set and the spatial distribution of calibration points can be selected.

Embodiments of the invention presented above are advantageous in that:

(1) The methods in some of the above embodiments only require the basic hardware setup with two eye cameras.

(2) For the 2-D gaze point estimation, the parallax and interpolation/extrapolation errors can be adequately compensated via designing a suitable regression model and training data acquisition process to collect an informative distribution of training data.

(3) For the 3-D gaze point estimation, the regression-based method can be used without the requirements of the knowledge of precise eyeball models and the calibration for the eye cameras.

(4) The method in some of the above embodiments can make eye tracking techniques accessible to eyewear users, which presents a significant portion of the entire population.

It will be appreciated by persons skilled in the art that numerous variations and/or modifications may be made to the invention as shown in the specific embodiments without departing from the spirit or scope of the invention as broadly described. The described embodiments of the invention should therefore be considered in all respects as illustrative, not restrictive. Any reference to prior art contained herein is not to be taken as an admission that the information is common general knowledge, unless otherwise indicated.

The invention claimed is:

1. A method for estimating gaze point, comprising:
obtaining data for determining training data, the obtaining including recording movement trajectories of pupil centers of a user's eyes and a movement trajectory of a calibration point in a scene image at a first calibration depth, the calibration point being gazed at by the user;
processing the training data;
determining one or more local-learning base gaze estimation models based on the processed training data, for determining one or both of: (i) 2D gaze points in a scene image and (ii) 3D gaze points in scene camera coordinates; and
applying the one or more local-learning base gaze estimation models in a gaze tracker for gaze estimation in a human-machine interaction.

2. The method of claim 1, further comprising determining 2D gaze points in the scene image.

3. The method of claim 1, further comprising determining 3D gaze points in the scene camera coordinates.

4. The method of claim 1, wherein the recording is performed as the user changes head pose.

5. The method of claim 1, wherein the recording is performed as the user rotates the head.

6. The method of claim 5, wherein the recording is performed for at least two rotations of the user's head.

7. The method of claim 1, wherein the obtaining further comprises obtaining 3D position of the calibration point.

8. The method of claim 1, wherein the obtaining further comprises recording, using the gaze tracker, movement trajectories of pupil centers of a user's eyes and movement trajectory of calibration point in a scene image at a second calibration depth different from the first calibration depth, the calibration point being gazed at by the user.

9. The method of claim 8, wherein the first calibration depth ($D_1$) and/or the second calibration depth ($D_2$) are selected based on a value of $1/D_1 - 1/D_2$.

10. The method of claim 8, wherein the recording is performed as the user changes head pose.

11. The method of claim 8, wherein the recording is performed as the user rotates the head.

12. The method of claim 11, wherein the recording is performed for at least two rotations of the user's head.

13. The method of claim 8, wherein obtaining the training data further comprises obtaining 3D position of the calibration point.

14. The method of claim 1, further comprising identifying eye smooth pursuit movement performed by the user during data recording, based on the data obtained.

15. The method of claim 14, further comprising preserving data recorded during eye smooth pursuit movement such that only said preserved data is included in the training data.

16. The method of claim 14, further comprising performing principal component analysis on the data obtained to identify eye smooth pursuit movement.

17. The method of claim 1, further comprising partitioning input space of a user's pupil center space into a plurality of sub-regions.

18. The method of claim 17, wherein determining one or more local-learning base gaze estimation models includes determining a local-learning base gaze estimation model for each of the sub-regions based on the processed training data.

19. The method of claim 18, wherein the determination of the local-learning base gaze estimation model is based on polynomial lens distortion model.

20. The method of claim 17, further comprising determining a coverage area of the sub-region.

21. The method of claim 20, wherein the sub-regions are rectangular.

22. The method of claim 20, wherein the sub-regions comprise multiple overlapping sub-regions.

23. The method of claim 20, wherein determining a coverage area of the sub-region comprises:
gradually expanding the coverage area to cover more training data; and
terminating the expansion process as the condition of reaching minimal leave-one-out prediction error.

24. The method of claim 20, further comprising determining eyeball center position and back-projection matrices for each of the sub-regions.

25. The method of claim 24, wherein the determination of the eyeball center position and back-projection matrices for each of the sub-regions is based on solving a constrained nonlinear optimization problem.

26. A method for estimating gaze point, comprising:
processing training data;
partitioning input space of a user's pupil center space into a plurality of sub-regions;
determining one or more local-learning base gaze estimation models based on the processed training data, for determining one or both of: (i) 2D gaze points in a scene image and (ii) 3D gaze points in scene camera coordinates, wherein determining one or more local-learning base gaze estimation models includes determining a local-learning base gaze estimation model for each of the sub-regions based on the processed training data and polynomial lens distortion model; and
applying the one or more local-learning base gaze estimation models in a gaze tracker for gaze estimation in a human-machine interaction.

27. The method of claim 26, further comprising determining 2D gaze points in the scene image and/or 3D gaze points in scene camera coordinates.

28. A method for estimating gaze point, comprising:
processing training data;
partitioning input space of a user's pupil center space into a plurality of sub-regions;
determining a coverage area of the sub-region, including
gradually expanding the coverage area to cover more training data; and
terminating the expansion process as the condition of reaching minimal leave-one-out prediction error;
determining one or more local-learning base gaze estimation models based on the processed training data, for determining one or both of: (i) 2D gaze points in a scene image and (ii) 3D gaze points in scene camera coordinates, wherein determining one or more local-learning base gaze estimation models includes determining a local-learning base gaze estimation model for the sub-region; and
applying the one or more local-learning base gaze estimation models in a gaze tracker for gaze estimation in a human-machine interaction.

29. The method of claim 28, further comprising determining 2D gaze points in the scene image and/or 3D gaze points in the scene camera coordinates.

30. A method for estimating gaze point, comprising:
processing training data;
partitioning input space of a user's pupil center space into a plurality of sub-regions;
determining a coverage area of the sub-region;
determining eyeball center position and back-projection matrices for each of the sub-regions;
determining one or more local-learning base gaze estimation models based on the processed training data, for determining one or both of: (i) 2D gaze points in a scene image and (ii) 3D gaze points in scene camera coordinates, wherein determining one or more local-learning base gaze estimation models includes determining a local-learning base gaze estimation model for each of the sub-regions; and
applying the one or more local-learning base gaze estimation models in a gaze tracker for gaze estimation in a human-machine interaction.

31. The method of claim 30, wherein the determination of the eyeball center position and back-projection matrices for each of the sub-regions is based on solving a constrained nonlinear optimization problem.

32. The method of claim 31, further comprising determining 3D gaze points in the scene camera coordinates.

* * * * *

UNITED STATES PATENT AND TRADEMARK OFFICE
CERTIFICATE OF CORRECTION

PATENT NO. : 11,181,978 B2
APPLICATION NO. : 16/442765
DATED : November 23, 2021
INVENTOR(S) : Youfu Li and Dan Su It is certified that error appears in the above-identified patent and that said Letters Patent is hereby corrected as shown below:

On the Title Page

Item (73), 'hemy8 SA, Morges (CH)' should read -- City University of Hong Kong, Kowloon (HK) --

Signed and Sealed this
Thirtieth Day of August, 2022

Katherine Kelly Vidal
*Director of the United States Patent and Trademark Office*